(12) United States Patent
Moon et al.

(10) Patent No.: US 10,380,718 B2
(45) Date of Patent: Aug. 13, 2019

(54) METHOD AND APPARATUS FOR DISPLAYING MEDICAL IMAGE

(71) Applicant: Samsung Electronics Co., Ltd., Suwon (KR)

(72) Inventors: Hee-yeon Moon, Hwaseong (KR); Sung-nam Kim, Seoul (KR); Byeong-won Lee, Suwon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 172 days.

(21) Appl. No.: 15/155,758

(22) Filed: May 16, 2016

(65) Prior Publication Data

US 2016/0350925 A1 Dec. 1, 2016

(30) Foreign Application Priority Data

May 27, 2015 (KR) ........................ 10-2015-0073925

(51) Int. Cl.
| | |
|---|---|
| *G06K 9/00* | (2006.01) |
| *G06T 3/40* | (2006.01) |
| *A61B 6/00* | (2006.01) |
| *G06T 3/20* | (2006.01) |
| *G06T 7/32* | (2017.01) |

(52) U.S. Cl.
CPC .......... *G06T 3/4038* (2013.01); *A61B 6/5241* (2013.01); *G06T 3/20* (2013.01); *G06T 7/32* (2017.01); *G06T 2207/10124* (2013.01)

(58) Field of Classification Search
None
See application file for complete search history.

(56) References Cited

U.S. PATENT DOCUMENTS

| | | | |
|---|---|---|---|
| 8,396,269 | B2 | 3/2013 | Henderson et al. |
| 9,430,706 | B1 * | 8/2016 | Peleg ................. G06K 9/00765 |
| 2003/0048938 | A1 * | 3/2003 | Wang ................... A61B 6/5241 |
| | | | 382/132 |
| 2003/0142787 | A1 * | 7/2003 | Jabri ................... A61B 6/4233 |
| | | | 378/98.12 |
| 2004/0114717 | A1 | 6/2004 | Kato |

(Continued)

FOREIGN PATENT DOCUMENTS

| | | |
|---|---|---|
| EP | 0 655 861 A1 | 11/1994 |
| EP | 2 554 119 A1 | 2/2013 |

(Continued)

OTHER PUBLICATIONS

Extended European Search Report dated Oct. 11, 2016 in corresponding European Patent Application No. 16170362.4.

*Primary Examiner* — Shervin K Nakhjavan
(74) *Attorney, Agent, or Firm* — Staas & Halsey LLP

(57) ABSTRACT

A method of displaying a medical image includes: obtaining a first image and a second image that are images of an object captured by using an X-ray; generating a synthesis image by overlapping a first overlapped region of the first image and a second overlapped region of the second image; obtaining information about synthesis accuracy representing a degree to which overlapped portions of the object represented by the first overlapped region and the second overlapped region coincide with each other; and displaying the information about the synthesis accuracy and the synthesis image together.

18 Claims, 28 Drawing Sheets

(56) References Cited

U.S. PATENT DOCUMENTS

| | | | | |
|---|---|---|---|---|
| 2005/0041041 | A1* | 2/2005 | Sakai | G06T 3/4038 345/629 |
| 2005/0213849 | A1* | 9/2005 | Kreang-Arekul | G06T 3/4038 382/284 |
| 2007/0098299 | A1* | 5/2007 | Matsumoto | G06T 15/08 382/284 |
| 2007/0140427 | A1* | 6/2007 | Jensen | A61B 6/481 378/98.12 |
| 2007/0165141 | A1* | 7/2007 | Srinivas | G06F 3/04845 348/571 |
| 2009/0257551 | A1* | 10/2009 | Dafni | A61B 6/022 378/6 |
| 2010/0014780 | A1* | 1/2010 | Kalayeh | G06T 1/00 382/284 |
| 2010/0138044 | A1* | 6/2010 | Maack | A61B 6/00 700/275 |
| 2010/0172472 | A1* | 7/2010 | Ermes | A61B 6/5241 378/62 |
| 2010/0202678 | A1* | 8/2010 | Kobayashi | G06T 7/70 382/132 |
| 2011/0181701 | A1* | 7/2011 | Varslot | G06T 7/0026 348/46 |
| 2011/0188726 | A1* | 8/2011 | Nathaniel | G01N 23/04 382/132 |
| 2013/0114790 | A1* | 5/2013 | Fabrizio | A61B 6/02 378/62 |
| 2013/0129168 | A1* | 5/2013 | Ross | G06T 7/0012 382/128 |
| 2013/0182008 | A1* | 7/2013 | Zhou | G06T 11/60 345/629 |
| 2013/0281825 | A1* | 10/2013 | Thiruvenkadam | G01R 33/56383 600/411 |
| 2013/0343523 | A1* | 12/2013 | Lee | A61B 6/4452 378/63 |
| 2014/0105357 | A1* | 4/2014 | Shin | A61B 6/4452 378/62 |
| 2014/0366057 | A1 | 12/2014 | Brockmann et al. | |
| 2015/0139514 | A1* | 5/2015 | Mohr | G06T 5/50 382/131 |
| 2015/0257846 | A1* | 9/2015 | Kubiak | A61B 6/487 600/407 |
| 2016/0135764 | A1* | 5/2016 | Wojcik | A61B 6/4233 378/62 |

FOREIGN PATENT DOCUMENTS

| | | |
|---|---|---|
| EP | 2 705 793 A1 | 3/2014 |
| JP | 2013-111445 | 6/2013 |
| WO | WO 2011/043458 A1 | 4/2011 |
| WO | WO 2014/132361 A1 | 9/2014 |

* cited by examiner

METHOD AND APPARATUS FOR DISPLAYING MEDICAL IMAGE

CROSS-REFERENCE TO RELATED APPLICATIONS

This application claims the benefit of foreign priority to Korean Patent Application No. 10-2015-0073925, filed on May 27, 2015, in the Korean Intellectual Property Office, the disclosure of which is incorporated herein in its entirety by reference.

BACKGROUND

1. Field

The present disclosure relates to methods and apparatuses for displaying a medical image, and more particularly, to methods and apparatuses for displaying a medical image, which display synthesis accuracy of a synthesis image in which a plurality of medical images are synthesized on the synthesis image.

2. Description of the Related Art

An apparatus for obtaining a medical image obtains medical image data regarding a fault, or a blood flow, etc. of an object by irradiating a predetermined signal toward the object and receiving a signal from the object in response to the irradiated signal.

For example, the apparatus for obtaining a medical image may obtain ultrasound image data, X-ray image data, computerized tomography (CT) image data, magnetic resonance (MR) image data, positron emission tomography (PET) image data, and image data similar thereto.

A region of an object, an image of which may be captured at one time by the apparatus for obtaining a medical image, may be limited to a portion of the object depending on the size of the apparatus, capturing accuracy, or an image resolution. Therefore, to obtain a synthesis image of a wider region or a higher resolution by coupling a plurality of captured images, an image stitching technique is used.

The apparatus for obtaining a medical image may divide an object of a long length, an image of which cannot be captured at one time, into a plurality of regions, and perform capturing a plurality of times. In this case, for image stitching, the apparatus for obtaining a medical image may set a plurality of regions whose images have been captured such that each of the plurality of regions whose images have been captured overlaps another region whose image has been captured.

A medical image system may generate a synthesis image for a wider region of an object by synthesizing a plurality of images of a plurality of regions of the object, whose images have bee captured, obtained by the apparatus for obtaining a medical image, and display the generated synthesis image on a screen of a medical image display device and provide the same to a user.

The image stitching technique is generally performed by a computer software, and a seamless image stitching result in which images overlap each other accurately is required.

However, in the case where the medical image system performs auto stitching that generates a synthesis image by automatically synthesizing a plurality of images, synthesis accuracy (that is, a degree to which portions of an object represented by regions in which a plurality of images overlap in order to generate a synthesis image coincide with each other) of a synthesis image may deteriorate due to an error of the apparatus, an error of an image analysis result, movement of an object, etc.

To accurately diagnose or treat a disease by using a synthesis image, the synthesis image in which a plurality of images are accurately synthesized without distortion should be provided to a user. Therefore, a method and an apparatus for displaying a medical image that display an overlapped section in which a plurality of images configuring a synthesis image overlap and synthesis accuracy of the synthesis image so that a user may intuitively recognize whether the synthesis image without distortion is provided are required.

SUMMARY

Provided are methods and apparatuses for displaying a medical image, which allow a user to intuitively recognize an overlapped section in which a plurality of images configuring a synthesis image overlap and synthesis accuracy of the synthesis image.

Additional aspects will be set forth in part in the description which follows and, in part, will be apparent from the description, or may be learned by practice of the presented embodiments.

According to an aspect of an embodiment, a method of displaying a medical image includes: obtaining a first image and a second image that are images of an object captured by using an X-ray; generating a synthesis image by overlapping a first overlapped region of the first image and a second overlapped region of the second image; obtaining information about synthesis accuracy representing a degree to which overlapped portions of the object represented by the first overlapped region and the second overlapped region coincide with each other; and displaying the information about the synthesis accuracy and the synthesis image together.

The obtaining of the information about the synthesis accuracy may include: obtaining the information about the synthesis accuracy by comparing a width of a region in which the first image overlaps the second image in order to generate the synthesis image with a reference value.

The first image may include a first ruler image representing information about a distance from a reference point to a portion of the object displayed in the first image, and the second image may include a second ruler image representing information about a distance from the reference point to a portion of the object displayed in the second image, and the obtaining of the information about the synthesis accuracy may further include: obtaining a first distance value displayed on one side of the first image included in the region in which the first image overlaps the second image, and a second distance value displayed on another side of the second image based on the first ruler image and the second ruler image; and determining a difference between the first distance value and the second distance value as the reference value.

The obtaining of the information about the synthesis accuracy may include: determining a similarity between the first overlapped region and the second overlapped region as the information about the synthesis accuracy by comparing the first overlapped region with the second overlapped region.

The generating of the synthesis image may include: displaying the first image including a first ruler image representing information about a distance from a reference point to a portion of the object displayed in the first image; displaying the second image including a second ruler image representing information about a distance from the reference point to a portion of the object displayed in the second image; comparing at least a portion of the first image with at least a portion of the second image based on the first ruler image and the second image; determining the first overlapped region and the second overlapped region based on a similarity between at least the portion of the first image with at least the portion of the second image; and generating a synthesis image by overlapping the first overlapped region of the first image and the second overlapped region of the second image.

The displaying of the information about the synthesis accuracy may include: comparing the synthesis accuracy with a threshold value; and displaying whether the synthesis accuracy is equal to or greater than the threshold value.

The displaying of the information about the synthesis accuracy may include: displaying a marker including at least one of a color, a pattern, a figure, a contrast, and a numerical value corresponding to the synthesis accuracy on a region in which the first image overlaps the second image in order to generate the synthesis image.

The displaying of the information about the synthesis accuracy may include: displaying the information about the synthesis accuracy according to a method selected based on a user input.

The method may further include: displaying a width of a region in which the first image overlaps the second image on the region in which the first image overlaps the second image in order to generate the synthesis image.

The generating of the synthesis image may include: generating the synthesis image by overlapping a plurality of images including the first image and the second image, and the method may further include: receiving a first user input of selecting a display mode for observing a plurality of overlapped regions in which the plurality of images overlap in order to generate the synthesis image; and magnifying the synthesis image based on a first overlapped region from among the plurality of overlapped regions.

The method may further include: receiving a second user input for moving between the plurality of overlapped regions; selecting a second overlapped region from among the plurality of overlapped regions based on the second user input; and magnifying the synthesis image based on the second overlapped region.

The method may further include: moving a location of the first image from among the first image and the second image configuring the synthesis image based on a user input; regenerating a synthesis image by overlapping the first image and the second image based on a location to which the first image has moved; obtaining information about synthesis accuracy with respect to the regenerated synthesis image; and displaying the synthesis accuracy with respect to the regenerated synthesis image on the regenerated synthesis image.

According to an aspect of another embodiment, an apparatus for displaying a medical image includes: a controller configured to obtain a first image and a second image that are images of an object captured by using an X-ray, generate a synthesis image by overlapping a first overlapped region of the first region and a second overlapped region of the second region, and obtain information about synthesis accuracy representing a degree to which overlapped portions of the object represented by the first overlapped region and the second overlapped region coincide with each other; and a display configured to display the information about the synthesis accuracy and the synthesis image together.

The controller may be configured to obtain the information about the synthesis accuracy by comparing a width of a region in which the first image overlaps the second image in order to generate the synthesis image with a reference value.

The first image may include a first ruler image representing information about a distance from a reference point to a portion of the object displayed in the first image, and the second image may include a second ruler image representing information about a distance from the reference point to a portion of the object displayed in the second image, and the controller may be configured to obtain a first distance value displayed on one side of the first image included in the region in which the first image overlaps the second image, and a second distance value displayed on the other side of the second image based on the first ruler image and the second ruler image, and determine a difference between the first distance value and the second distance value as the reference value.

The controller may be further configured to determine a similarity between the first overlapped region and the second overlapped region as the information about the synthesis accuracy by comparing the first overlapped region with the second overlapped region.

The controller may be further configured to control the display to display the first image including a first ruler image representing information about a distance from a reference point to the first image, and display the second image including a second ruler image representing information about a distance from the reference point to the second image, compare at least a portion of the first image with at least a portion of the second image based on the first ruler image and the second ruler image, determine the first overlapped region and the second overlapped region based on a similarity between at least the portion of the first image with at least the portion of the second image, and generate a synthesis image by overlapping the first overlapped region of the first image and the second overlapped region of the second image.

The controller may be further configured to control the display to compare the synthesis accuracy with a threshold value, and display whether the synthesis accuracy is equal to or greater than the threshold value.

The display may be further configured to display a marker including at least one of a color, a pattern, a figure, a contrast, and a numerical value corresponding to the synthesis accuracy on a region in which the first image overlaps the second image in order to generate the synthesis image.

The apparatus may further include: a user input configured to receive a user input, wherein the controller may be further configured to display the information about the synthesis accuracy according to a method selected based on the user input.

The display may be further configured to display a width of a region in which the first image overlaps the second image on the region in which the first image overlaps the second image in order to generate the synthesis image.

The apparatus may further include: a user input unit configured to receive a user input, wherein the controller may be further configured to generate the synthesis image by overlapping a plurality of images including the first image and the second image, and when receiving a first user input of selecting a display mode for observing a plurality of overlapped regions in which the plurality of images overlap in order to generate the synthesis image, control the display to magnify the synthesis image based on a first overlapped region from among the plurality of overlapped regions.

When receiving a second user input for moving between the plurality of overlapped regions, the controller may be further configured to control the display to select a second overlapped region from among the plurality of overlapped regions based on the second user input, and magnify the synthesis image based on the second overlapped region.

The controller may be further configured to move a location of the first image from among the first image and the second image configuring the synthesis image based on a user input, regenerate a synthesis image by overlapping the first image and the second image based on a location to which the first image has moved, obtain information about synthesis accuracy with respect to the regenerated synthesis image, and control the display to display the synthesis accuracy with respect to the regenerated synthesis image on the regenerated synthesis image.

According to an aspect of another embodiment, a non-transitory computer-readable recoding medium having recorded thereon, a program for executing a method of displaying a medical image, the program includes: obtaining a first image and a second image that have repeatedly captured the same region of an object; generating a synthesis image by overlapping a first overlapped region of the first image and a second overlapped region of the second image; obtaining information about synthesis accuracy representing a degree in which a first portion of the object represented by the first overlapped region and a second portion of the object represented by the second overlapped region coincide with each other; and displaying the information about the synthesis accuracy on the synthesis image.

According to an aspect of another embodiment, an apparatus for displaying a medical image comprises: a controller configured to: obtain a first image, of a first region of an object, captured using an X-ray detector positioned at a first position distanced from a reference point by a first distance, obtain a second image, of a second region of the object, captured using the X-ray detector positioned at a second position distanced from the reference point by a second distance, the first region having an overlap with the second region, generate a synthesis image by overlapping a first image region of the first image and a second image region of the second image, and obtain information about synthesis accuracy, which represents a degree to which the first image region and the second image region coincide with each other in representing a portion of the object within the overlap of the first region with the second region, by comparing the overlap distance with a reference distance value determined based on the first and second distances of the X-ray detector from the reference point, a display configured to display the information about the synthesis accuracy and the synthesis image together.

The reference distance value is a distance between a location on one side of the X-ray detector when positioned at the first position, and a location on an another side of the X-ray detector when positioned at the second position.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
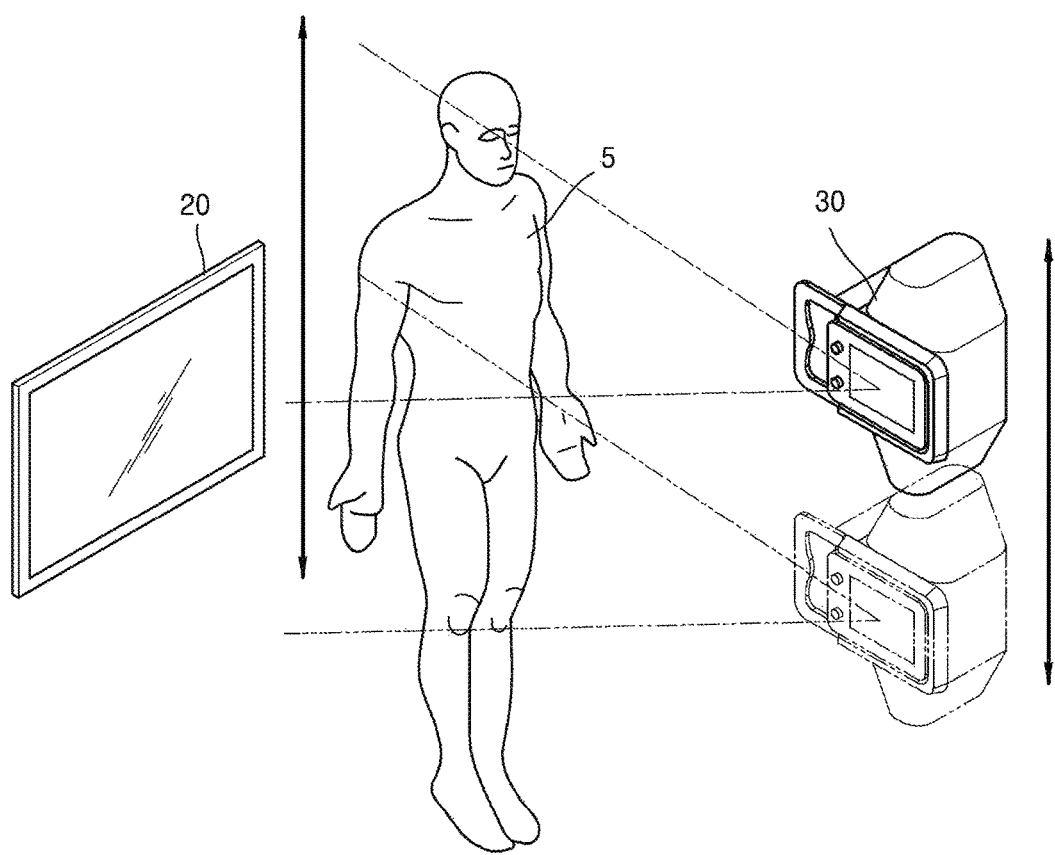
FIG. 1 is a diagram for explaining an operation of an apparatus for obtaining a medical image, which obtains images of a plurality of regions of an object as an X-ray irradiator moves, according to an embodiment.

Reference will now be made in detail to the embodiments, examples of which are illustrated in the accompanying drawings, wherein like reference numerals refer to the like elements throughout. The embodiments are described below to explain the present invention by referring to the figures.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the present disclosure.

Throughout the specification, it will also be understood that when a component "includes" an element, unless there is another opposite description thereto, it should be understood that the component does not exclude another element and may further include another element. In addition, terms such as " ... unit", " ... module", or the like refer to units that perform at least one function or operation, and the units may be implemented as hardware or software or as a combination of hardware and software.

Throughout the specification, it will be understood that when a certain component is referred to as being "connected" to another component, it may be "directly connected" to the other component, or may be "electrically connected" to the other component with other component interposed therebetween. When a part "includes" or "comprises" an element, unless there is a particular description contrary thereto, the part can further include other elements, not excluding the other elements.

In the present specification, a "value A corresponds to a value B" may denote that the value A is the same as, or substantially the same as, or proportional to the value B. For example, in the case where the value A is proportional to the value B, the value B may be obtained by multiplying the value A by a predetermined coefficient. In the case where the value A is substantially the same as the value B, a difference between the value A and the value B may be within a predetermined range.

Furthermore, in the present specification, an "object" may be a human, an animal, or a part of a human or animal. For example, the object may include an organ such as a liver, a heart, a womb, a brain, a breast, and an abdomen, a cell, a tissue, or a blood vessel. Also, the "object" may include a phantom. The phantom denotes a material having a volume very similar to the density of living things and an effective atomic number.

In the present specification, a "user" denotes a medical expert and may be a doctor, a nurse, a medical technologist, a medical image expert, a radiological technologist, a sonographer, an engineer repairing a medical instrument, etc., but is not limited to a medical expert. For example, a "user" may be an ordinary person who uses an apparatus for displaying a medical image, and may be a patient himself.

Throughout the specification, a "medical image" may include all images for diagnosing and treating a disease, representing the cross-section and volume data regarding an object from a signal projected to the object. For example, a "medical image" may include an ultrasound image, a magnetic resonance imaging (MRI) image, a computerized tomography (CT) image, an X-ray image, or a positron emission tomography (PET) image, etc. Also, a "medical image" may include all of a two-dimensional (2D) image for the cross-section of an object, a three-dimensional (3D) image for the space of an object, a moving image, and a stereo image that allows a viewer to feel a sense of depth.

Reference will now be made in detail to embodiments, examples of which are illustrated in the accompanying drawings. In this regard, the present embodiments may have different forms and should not be construed as being limited to the descriptions set forth herein. Also, for clarity of description in the drawings, portions irrelevant to the description have been omitted, and like reference numerals are used for like parts throughout the specification.

An apparatus for obtaining a medical image obtains medical image data regarding a fault or a blood flow, etc. of an object by irradiating a predetermined signal toward the object and receiving a signal from the object in response to the irradiated signal.

For example, an apparatus for obtaining a medical image may obtain ultrasound image data, X-ray image data, CT image data, magnetic resonance (MR) image data, PET image data, and similar image data.

A region of an object, whose image may be captured at one time by an apparatus for obtaining a medical image may be limited to a portion of the object depending on the size, capturing accuracy, or image resolution of the apparatus. Therefore, the apparatus for obtaining a medical image may divide an object having a long length that cannot be captured at one time into a plurality of regions, images of which are captured, and perform capturing a plurality of times.

The apparatus for obtaining a medical image may set a plurality of regions whose images are captured so that each of the plurality of regions whose images are captured may overlap another region whose image is captured. For example, the apparatus for obtaining a medical image may include an X-ray capturing apparatus that obtains X-ray image data.

An X-ray has a characteristic of attenuating depending on the property and the distance of an object when passing through the arbitrary object. An X-ray capturing apparatus that may examine an internal shape of an object by using this characteristic is widely used for non-destructive examination for a medical use or an industrial use.

FIG. 1 is a diagram for explaining an operation of an apparatus for obtaining a medical image, which obtains images of a plurality of regions of an object as an X-ray irradiator moves, according to an embodiment As illustrated in FIG. 1, an X-ray capturing apparatus includes the X-ray irradiator 30 that emits an X-ray to an object 5, and a detector 20 that detects an X-ray that has passed through the object. The X-ray capturing apparatus may capture images of a plurality of regions of the object 5 while moving the X-ray irradiator 30 and the detector 20 together.

The X-ray capturing apparatus may divide the object 5 into a plurality of regions whose images are captured along a predetermined direction, move the X-ray irradiator 30 and the detector 20 to a location of each region whose image is captured, and obtain an image of each region whose image is captured. The image of each region of the object 5 may be obtained such that a portion of the region overlaps an image of another region whose image is captured.

As illustrated in FIG. 1, after obtaining a first image of a first region of the object 5, the X-ray capturing apparatus may move the X-ray irradiator 30 and the detector 20 along a predetermined direction. Also, the X-ray capturing apparatus may obtain a second image of a second region of the object 5.

Figure 2:
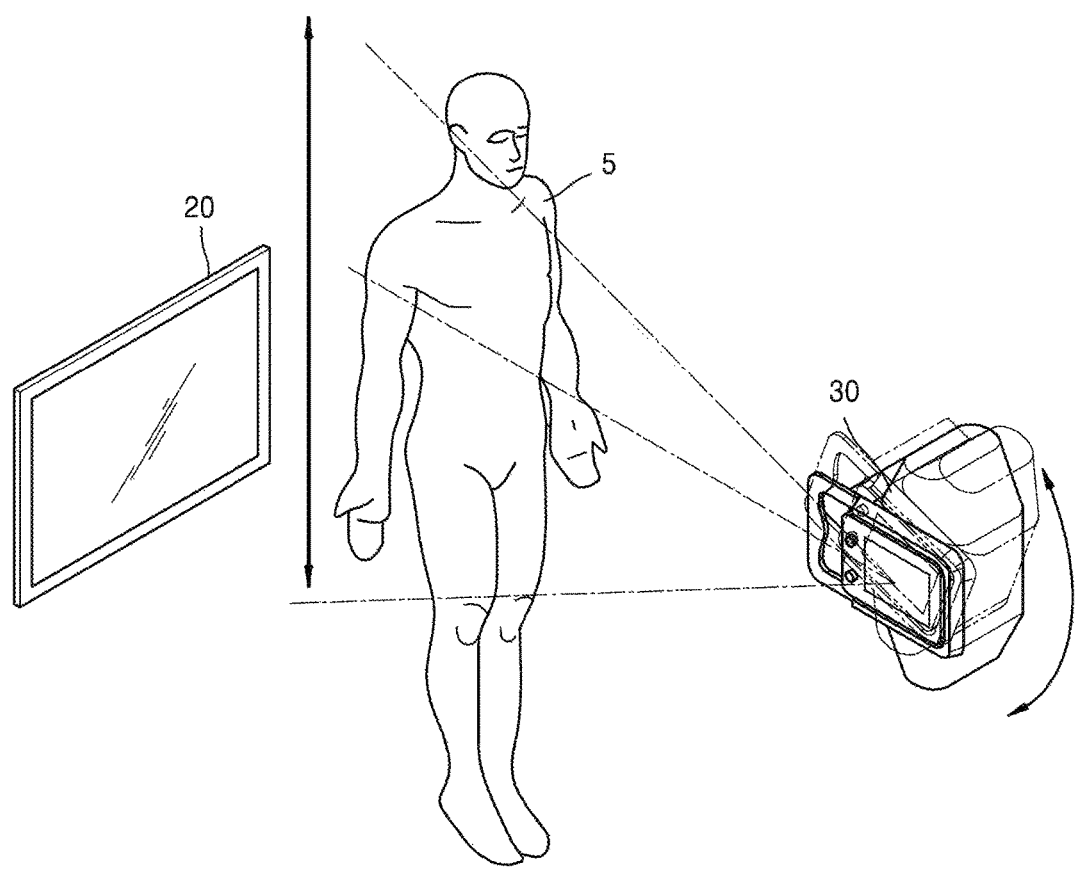
FIG. 2 is a diagram for explaining an operation of an apparatus for obtaining a medical image, which obtains images of a plurality of regions of an object as an X-ray irradiator rotates, according to an embodiment.

Meanwhile, FIG. 2 is a diagram for explaining an operation of an apparatus for obtaining a medical image, which obtains images of a plurality of regions of an object as an X-ray irradiator rotates, according to an embodiment.

As illustrated in FIG. 2, the X-ray capturing apparatus may divide the object 5 into a plurality of regions along a predetermined direction, rotate the X-ray irradiator 30 by a rotation angle corresponding to each region, move the detector 20 to a location corresponding to each region, and then obtain an image of each region. An image of each region of the object 5 may be obtained such that portions of regions overlap each other.

After obtaining a first image of a first region of the object 5, the X-ray capturing apparatus may rotate the X-ray irradiator 30, and move the detector 20 along a predetermined direction. Also, the X-ray capturing apparatus may obtain a second image of a second region of the object 5.

Though FIGS. 1 and 2 illustrate an example of obtaining images of two regions of the object 5, it will be obvious to a person of ordinary skill in the art that images of various numbers of regions of the object 5 may be obtained by the X-ray capturing apparatus. The X-ray capturing apparatus may capture a wide region of the object by performing capturing a plurality of number of times.

A user may designate a capturing start region and a capturing end region of an object by moving or rotating the X-ray irradiator 30 of the X-ray capturing apparatus. The X-ray irradiator 30 may calculate a distance (for example, mm value) from a capturing start region to a capturing end region of an object and transmit the calculated distance to a workstation. The X-ray capturing apparatus may determine a region ranging from a capturing start region to a capturing end region as a region.

The workstation of the X-ray capturing apparatus may determine a number of images to be captured within a captured section and a width (an overlap width) of a region (an image overlap region) in which each region overlaps the next region. For image stitching, the workstation may control the X-ray capturing apparatus so that each of a plurality of regions may overlap another region.

A medical image system that supports an image stitching technique may generate a synthesis image of a wider region of an object by synthesizing a plurality of images of a plurality of regions of the object obtained from an apparatus for obtaining a medical image. The medical image system may display a synthesis image on a screen of a medical image display device and provide the same to a user.

Figure 3:
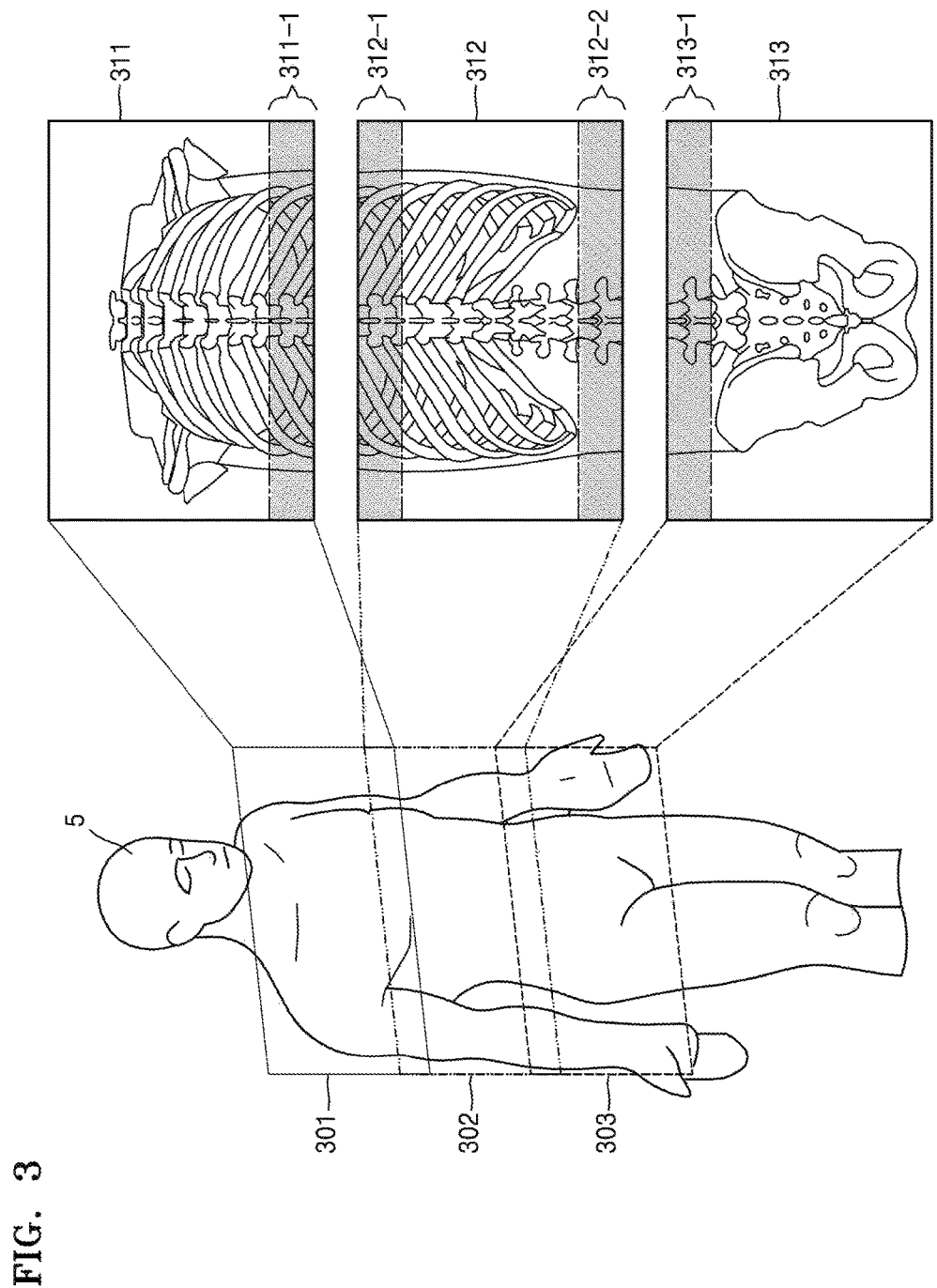
FIGS. 3 and 4 are diagrams for explaining an image stitching technique of obtaining a synthesis image for a wide region of an object by combining a plurality of captured images.
Figure 4:
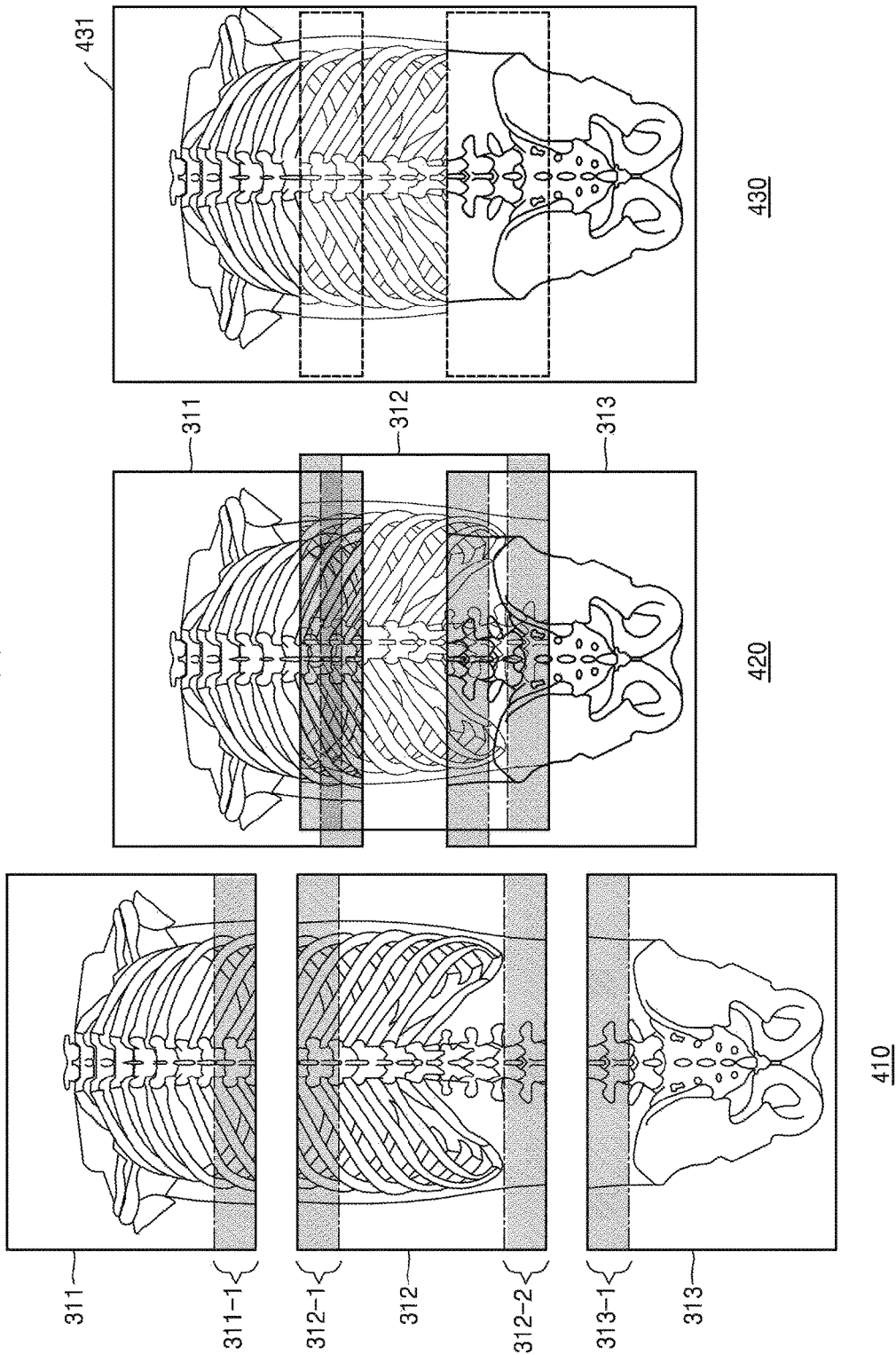

FIGS. 3 and 4 are diagrams for explaining an image stitching technique of obtaining a synthesis image for a wide region of an object by combining a plurality of captured images.

As illustrated in FIG. 3, an apparatus for obtaining a medical image may divide the object 5 of a long length that cannot be captured at one time into a plurality of regions 301, 302, and 303, and perform capturing a plurality of number of times. For image stitching, the apparatus for obtaining a medical image may set a plurality of regions so that each of the plurality of regions 301, 302, and 303 may overlap another region.

The apparatus for obtaining a medical image may obtain a plurality of images 311, 312, and 313 of the plurality of regions 301, 302, and 303. For example, the apparatus for obtaining a medical image may obtain the first image 311 of the first region 301, the second image 312 of the second region 302, and the third image 313 of the third region 303.

As illustrated in FIG. 3, the first image 311 and the second image 312 may include overlapped regions (image regions) 311-1 and 312-1 representing a region in which the first region 301 overlaps the second region 302. Also, the second image 312 and the third image 313 may include overlapped regions 312-2 and 313-1 representing a region in which the second region 302 overlaps the third region 303.

An image 410 of FIG. 4 illustrates the plurality of images 311, 312, and 313 obtained by repeatedly capturing the same region of an object.

As illustrated in images 420 and 430 of FIG. 4, the medical image system may generate a synthesis image 431 so that at least portions of medical images may overlap each other. The medical image system may generate the synthesis image 431 so that at least portions of medical images may overlap each other based on location information of medical images of adjacent regions, or based on results of comparing the medical images of the adjacent regions.

However, in the case where the medical image system performs auto stitching, synthesis accuracy (that is, a degree in which portions of an object represented by regions in which a plurality of images overlap in order to generate a synthesis image coincide with each other) of the synthesis image 431 may deteriorate due to an error of an apparatus, an error of image analysis results, or the movement of the object.

As illustrated in the image 420 of FIG. 4, the medical image system may deviate from the overlapped region 311-1 of the first image 311 and the overlapped region 312-1 of the second image 312 representing the same portion of an object, and erroneously overlap the first image 311 and the second image 312. Also, the medical image system may deviate from the overlapped region 312-2 of the second image 312 and the overlapped region 313-1 of the third image 313 representing the same portion of the object, and erroneously overlap the second image 312 and the third image 313.

As illustrated in the image 430 of FIG. 4, the medical image system may generate the synthesis image 431 having low synthesis accuracy.

To accurately diagnose or treat a disease by using a synthesis image, the synthesis image in which a plurality of images are accurately synthesized without distortion should be provided to a user. Also, a user should be able to intuitively recognize whether a synthesis image without distortion is provided.

Therefore, embodiments provide an apparatus and a method of displaying a medical image that allow a user to intuitively recognize an overlapped section in which a plurality of images configuring a synthesis image overlap each other, and synthesis accuracy with respect to the synthesis image.

Figure 5:
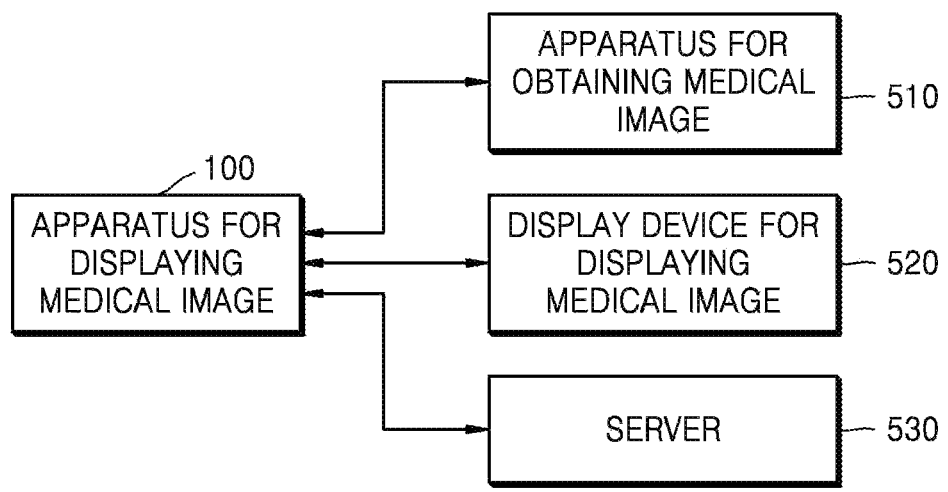
FIG. 5 is a block diagram illustrating an apparatus for displaying a medical image, which receives medical image data from various devices, according to an embodiment.

FIG. 5 is a block diagram illustrating an apparatus 100 for displaying a medical image, which receives medical image data from various devices according to an embodiment.

According to an embodiment, the apparatus 100 for displaying a medical image may receive medical image data stored therein or medical image data stored in various devices, and display a medical image generated by using the received medical image data.

For example, the apparatus 100 for displaying a medical image may display an ultrasound image, an X-ray image, a CT image, an MR image, a PET image, etc. A medical image displayed via the apparatus 100 for displaying a medical image may be used for diagnosing or treating a patient's disease.

The apparatus 100 for displaying a medical image may receive medical image data regarding a plurality of regions of an object, and generate a plurality of images of the plurality of regions of the object by using the received medical image data. The apparatus 100 for displaying a medical image may generate a synthesis image of a wider region of the object by synthesizing a plurality of images, and display the generated synthesis image.

The apparatus 100 for displaying a medical image according to an embodiment may be a mobile device implemented as a portable type. Also, the apparatus 100 for displaying a medical image may be an apparatus attached to another device or fixed to a predetermined location. The apparatus 100 for displaying a medical image may be an apparatus manufactured for only diagnosing or treating a disease, but is not limited thereto, and may include various apparatuses that may display an image such as a smartphone, a laptop computer, a personal digital assistant (PDA), a tablet personal computer (PC), an electronic book terminal, a terminal for digital broadcasting, a portable multimedia player (PMP), a navigation apparatus, a smart TV, and consumer electronics.

According to an embodiment, the apparatus 100 for displaying a medical image may be connected, via a wired line or wirelessly, with various devices 510, 520, and 530 that provide medical image data regarding an object such as an apparatus 510 for obtaining a medical image, a medical image display device 520, or a server 530.

According to an embodiment, the apparatus 100 for displaying a medical image may receive medical image data from the various devices 510, 520, and 530. The apparatus 100 for displaying a medical image displays a medical image generated by using the received medical image data. The apparatus 100 for displaying a medical image may display not only a medical image but also various information processed by the various devices 510, 520, and 530 via a graphic user interface (GUI). The information processed by the apparatus 100 for displaying a medical image may include information related to a function and/or a parameter used for the apparatus 100 for displaying a medical image to display a medical image, and include information for controlling the various devices 510, 520, and 530.

According to an embodiment, the apparatus 100 for displaying a medical image may transmit a control signal to the various devices 510, 520, and 530. The apparatus 510 for obtaining a medical image may irradiate a predetermined signal toward an object according to a control signal transmitted from the apparatus 100 for displaying a medical image, and obtain medical image data regarding a fault or blood flow, etc. of the object by receiving a signal from the object in response to the irradiated signal.

For example, the apparatus 100 for displaying a medical image may be connected, via a wired line or wirelessly, with an X-ray capturing apparatus that obtains an X-ray image serving as the apparatus 510 for obtaining a medical image. The apparatus 100 for displaying a medical image may exist in a space physically separated from the X-ray capturing apparatus and control the X-ray capturing apparatus.

Alternatively, the medical image display device 520 may obtain medical image data regarding an object according to a control signal transmitted from the apparatus 100 for displaying a medical image, or display a medical image of the object. The server 530 may obtain medical image data regarding the object from the apparatus 510 for obtaining a medical image, a memory, or another server according to a control signal transmitted from the apparatus 100 for displaying a medical image.

A method of displaying information about synthesis accuracy on a synthesis image in an apparatus for displaying a medical image according to an embodiment is described below with reference to FIG. 6.

Figure 6:
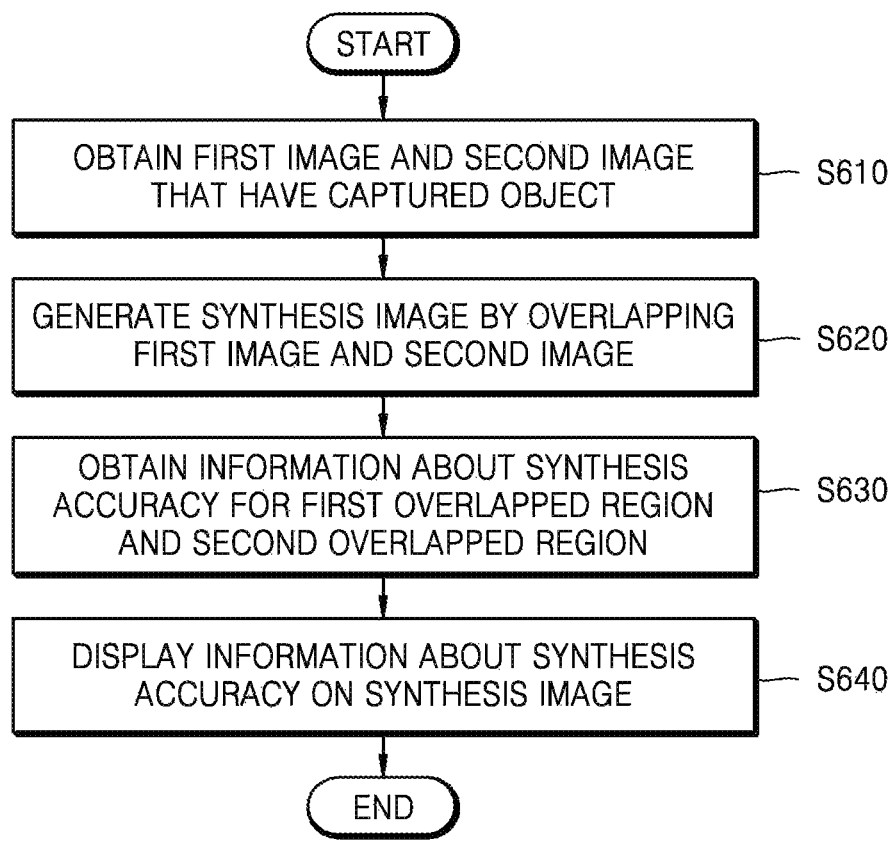
FIG. 6 is a flowchart illustrating a method of displaying information about synthesis accuracy on a synthesis image in an apparatus for displaying a medical image, according to an embodiment.

FIG. 6 is a flowchart illustrating a method of displaying information about synthesis accuracy on a synthesis image in an apparatus 100 for displaying a medical image according to an embodiment.

In operation S610, according to an embodiment, the apparatus 100 for displaying a medical image may obtain a first image and a second image that have captured an object. For example, the apparatus 100 for displaying a medical image may obtain the first image and the second image that have captured the object by using an X-ray. The first image and the second image may be images that have repeatedly captured a predetermined region of the object.

For example, the apparatus 100 for displaying a medical image may be connected with the apparatus for obtaining a medical image and obtain an image of the object from the apparatus for obtaining a medical image.

The apparatus for obtaining a medical image may obtain medical image data regarding the object by irradiating a predetermined signal toward the object and receiving a signal from the object in response to the irradiated signal. The apparatus 100 for displaying a medical image may obtain the first image and the second image of the object from the medical image data obtained from the apparatus for obtaining a medical image.

The apparatus for obtaining a medical image may divide the object into a plurality of regions along a predetermined direction, and obtain a plurality of images corresponding to the plurality of regions.

The apparatus for obtaining a medical image may determine a captured section based on a user input that designates a capturing start region and a capturing end region of the object. For example, in the case of intending to obtain a plurality of images of a region ranging from a first point to a second point of the object, the apparatus for obtaining a medical image may receive a user input that designates a region including the first point as a capturing start region and designates a region including the second point as a capturing end region. The apparatus for obtaining a medical image may determine a region ranging from the capturing start region to the capturing end region as a captured section.

The apparatus for obtaining a medical image may determine a number of images to be captured within the captured section, and a width of a region in which each region overlaps the next region. For image stitching, the apparatus for obtaining a medical image may set a plurality of regions so that each of the plurality of regions may overlap another region.

For another example, the apparatus 100 for displaying a medical image may obtain the first image and the second image from a memory provided to the inside, a memory of an external device, or an external server.

The first image and the second image may be images that have captured the first region and the second region of the object, respectively. The first region and the second region may be set so that portions of the first region and the second region may overlap each other.

The first image and the second image may include a ruler image representing information about the location of each image. The ruler image may represent information about a distance from a reference point to a portion of an object displayed on an image. The ruler image may include information about a distance from the reference point to one side of an image, and a distance from the reference point to the other side of the image.

A ruler image included in each image may be an image that has captured a lead ruler put beside an object, or a virtual ruler image generated based on information obtained from the apparatus for obtaining a medical image.

In the case where the first image and the second image are X-ray images, the apparatus 100 for displaying a medical image may obtain information about a distance from the reference point to a portion of an object displayed on an image based on at least one of information about the location of the X-ray irradiator that obtains images, information about a rotational angle of the X-ray irradiator, information about the location of the detector, and information about the size of the detector. The apparatus 100 for displaying a medical image may generate a virtual ruler image based on the obtained information. The apparatus 100 for displaying a medical image may receive location information of the detector when capturing an image from the X-ray capturing apparatus, and generate a virtual ruler image based on the location information of the detector.

For example, a distance from the reference point to one side of an image, and a distance from the reference point to the other side of the image may respectively correspond to a distance from the reference point to one side of an X-ray detector of a location for obtaining an image, and a distance from the reference point to the other side of the X-ray detector of a location for obtaining the image. The reference point may correspond to one side of the X-ray detector when the X-ray detector is located at a reference location. A reference location may be determined in advance as a default value, or determined by a user input.

The apparatus 100 for displaying a medical image may obtain a plurality of images equal to or greater than three images including the first image and the second image. The apparatus 100 for displaying a medical image may obtain at least three images of at least three regions of an object. Each of the at least three regions of the object may be set so that a portion of the each region may overlap another region.

In operation S620, the apparatus 100 for displaying a medical image may generate a synthesis image by synthesizing the first image and the second image.

The apparatus 100 for displaying a medical image may provide an auto stitching function to a user. When receiving a user input that orders to perform auto stitching, the apparatus 100 for displaying a medical image may automatically synthesize the first image and the second image.

The apparatus 100 for displaying a medical image may generate a synthesis image by overlapping portions of the first image and the second image. The apparatus 100 for displaying a medical image may determine a first overlapped region within the first image and a second overlapped region within the second image. The apparatus 100 for displaying a medical image may generate a synthesis image by overlapping the first overlapped region of the first image and the second overlapped region of the second image.

The apparatus 100 for displaying a medical image may generate a synthesis image so that at least portions of images may overlap each other based on location information of the images or based on results of comparing the images. The apparatus 100 for displaying a medical image may generate a synthesis image so that at least portions of medical images overlap each other based on location information of images of adjacent regions, or based on results of comparing the images of the adjacent regions.

For example, in the case where the first image and the second image are X-ray images, the apparatus 100 for displaying a medical image may dispose the first image and the second image so that portions of the first image and the second image may overlap each other based on location information of the detector when capturing each image and results of comparing the images, and synthesize the first image and the second image.

For example, the apparatus 100 for displaying a medical image may generate a synthesis image of the first image and the second image based on location information of the images.

The apparatus 100 for displaying a medical image may synthesize images based on a ruler image representing information about the location of each image.

The apparatus 100 for displaying a medical image may obtain location information of an image based on a ruler image included in the image. The ruler image included in the image may be a captured image of a lead ruler put beside an object, or a virtual ruler image generated based on information obtained from the apparatus for obtaining a medical image. The apparatus 100 for displaying a medical image may synthesize the first image and the second image by overlapping points having the same value on a first ruler image of the first image and a second ruler image of the second image.

Alternatively, the apparatus 100 for displaying a medical image may obtain relative location information of an image based on the width of a region in which each region overlaps another region.

The information about the relative location of an image may include information about the location of a region corresponding to the relevant image with respect to a region corresponding to another image. For example, information about the location of the first image may include information about the location of a region corresponding to the first image with respect to a region corresponding to the second image. That is, the information about the location of the first image may include information about the width of a region in which a first region overlaps a second region.

The apparatus 100 for displaying a medical image may synthesize the first image and the second image by overlapping points having the same location information within the first image and the second image.

For another example, the apparatus 100 for displaying a medical image may compare images and generate a synthesis image of the first image and the second image based on a result of the comparison. The apparatus 100 for displaying a medical image may determine overlapped regions whose images are captured images of the same portion of an object by comparing images.

The apparatus 100 for displaying a medical image may compare the first image with the second image, and calculate a similarity between a portion of the first image and a portion of the second image. The apparatus 100 for displaying a medical image may determine a first overlapped region within the first image and a second overlapped region within the second image based on the similarity between a portion of the first image and a portion of the second image.

For example, the apparatus 100 for displaying a medical image may divide the first image and the second image into a plurality of regions, and calculate a similarity between each region of the first image and each region of the second region. The apparatus 100 for displaying a medical image may determine a region of the first image that has a highest similarity and a region of the second image that has a highest similarity as the first overlapped region and the second overlapped region, respectively.

The apparatus 100 for displaying a medical image may further take into account location information of images in generating a synthesis image based on a result of comparing the images. The apparatus 100 for displaying a medical image may reduce a load of an amount of calculation when comparing the entire region of the first image with the entire region of the second image, and raise a processing speed by comparing only neighboring regions of points having the same location information within the first image and the second image.

A specific method of automatically synthesizing the first image and the second image in the apparatus 100 for displaying a medical image is described below with reference to FIGS. 7A to 7C.

In operation S630, the apparatus 100 for displaying a medical image according to an embodiment may obtain information about synthesis accuracy of the synthesis image generated in operation S620.

The synthesis accuracy may represent a degree in which overlapped portions represented by the first overlapped region of the first image configuring the synthesis image and the second overlapped region of the second image configuring the synthesis image coincide with each other. According to an embodiment, the synthesis accuracy may represent a degree in which a first portion of an object represented by the first overlapped region of the first image configuring the synthesis image and a second portion of the object represented by the second overlapped region of the second image configuring the synthesis image coincide with each other.

Information about the synthesis accuracy may include a digitized value of the synthesis accuracy. Alternatively, the information about the synthesis accuracy may include information as to whether synthesis of images is successful. For example, the apparatus 100 for displaying a medical image may compare a digitized value of the synthesis accuracy with a threshold value, and determine whether synthesis of images is successful based on a result of the comparison.

For example, the apparatus 100 for displaying a medical image may obtain information about synthesis accuracy by comparing the width of a region in which the first image overlaps the second image in order to generate a synthesis image with a reference value. The width of the region in which the first image overlaps the second image in order to generate the synthesis image corresponds to the width of the first overlapped region determined within the first image or the second overlapped region determined within the second image.

For example, in the case where the first image and the second image are X-ray images, the apparatus 100 for displaying a medical image may obtain information about the synthesis accuracy by allowing the detector to compare the width (that is, the width of a region in which the first image overlaps the second image) of a region in which images configuring the synthesis image overlap each other with the width (a reference value) of an overlapped region when the images are captured.

The apparatus 100 for displaying a medical image may obtain a difference value between the width of the region in which the first image overlaps the second image and the reference value as the information about the synthesis accuracy. Alternatively, the apparatus 100 for displaying a medical image may obtain a ratio by which the difference value between the width of the region in which the first image overlaps the second image and the reference value deviates from an error of the system as the information about the synthesis accuracy.

The apparatus 100 for displaying a medical image may determine that the synthesis accuracy is high when the difference value between the width of the region in which the first image overlaps the second image and the reference value is small. Alternatively, the apparatus 100 for displaying a medical image may determine that the first image and the second image have been successfully synthesized in the case where the difference value between the width of the region in which the first image overlaps the second image and the reference value is equal to or less than the error of the system. The apparatus 100 for displaying a medical image may determine that synthesis of the first image and the second image has failed in the case where the difference value between the width of the region in which the first image overlaps the second image and the reference value is greater than the error of the system.

The apparatus 100 for displaying a medical image may determine the reference value based on location information of images. The apparatus 100 for displaying a medical image may determine the reference value based on information about a distance from a reference point to a portion of an object displayed on an image.

The apparatus 100 for displaying a medical image may determine a reference value based on a ruler image included in an image. The apparatus 100 for displaying a medical image may obtain a first distance value displayed on one side of the first image included in an overlapped region and a second distance value displayed on the other side of the second image included in the overlapped region based on a first ruler image of the first image and a second ruler image of the second image. The apparatus 100 for displaying a medical image may determine a difference between the first distance value and the second distance value as the reference value.

Alternatively, the apparatus 100 for displaying a medical image may determine the width of a region in which each region overlaps another region as the reference value in allowing the apparatus for obtaining a medical image to obtain a plurality of images of a plurality of regions of an object. The width of the region in which each region overlaps another region may be determined in advance as a default value, or determined by a user input, or measured by the apparatus for obtaining a medical image.

For another example, the apparatus 100 for displaying a medical image may obtain a similarity between the first overlapped region and the second overlapped region as the information about the synthesis accuracy by comparing the first overlapped region with the second overlapped region.

The apparatus 100 for displaying a medical image may determine that the synthesis accuracy is high when the similarity between the first overlapped region and the second overlapped region is high. Alternatively, the apparatus 100 for displaying a medical image may determine that the first image and the second image have been successfully synthesized in the case where the similarity between the first overlapped region and the second overlapped region is equal to or greater than a threshold value. The apparatus 100 for displaying a medical image may determine that synthesis of the first image and the second image has failed in the case where the similarity between the first overlapped region and the second overlapped region is less than the threshold value.

A method of obtaining the information about the synthesis accuracy in the apparatus 100 for displaying a medical image is described below with reference to FIGS. 8 to 11.

In operation S640, the apparatus 100 for displaying a medical image may display the information about the synthesis accuracy and the synthesis image together. For example, the apparatus 100 for displaying a medical image may display the information about the synthesis accuracy on the synthesis image.

The apparatus 100 for displaying a medical image may display the information about the synthesis accuracy on a region in which the first image overlaps the second image in order to generate the synthesis image.

The apparatus 100 for displaying a medical image may display the synthesis accuracy by using at least one of color, a pattern, a figure, contrast, and a numerical value on a region in which the first image overlaps the second image in order to generate the synthesis image. For example, the apparatus 100 for displaying a medical image may display a marker including at least one of color, a pattern, a figure, contrast, and a numerical value corresponding to the synthesis accuracy on the region in which the first image overlaps the second image.

In consideration of the case where the apparatus 100 for displaying a medical image supports only black and white display, or the case where a user is a color-blind person, the apparatus 100 for displaying a medical image may display the information about the synthesis accuracy by differing a pattern filling the marker. For example, the apparatus 100 for displaying a medical image may display a complicated pattern filling the maker when the synthesis accuracy is low.

The apparatus 100 for displaying a medical image may display the information about the synthesis accuracy according to a selected method based on a user input.

The apparatus 100 for displaying a medical image may display differently an overlapped region in which it is determined that two images have been successfully synthesized, and an overlapped region in which it is not determined that two images have been successfully synthesized. The apparatus 100 for displaying a medical image may determine whether two images have been successfully synthesized by comparing the synthesis accuracy with a threshold value. The apparatus 100 for displaying a medical image may display differently an overlapped region in which it is determined that two images have been successfully synthesized, and an overlapped region in which it is not determined that two images have been successfully synthesized by displaying whether the synthesis accuracy is equal to or greater than a threshold value. The threshold value may be determined in advance as a default value, or may be a value set based on a user input.

For example, in the case where the synthesis accuracy of the region in which the first image overlaps the second image is equal to or greater than the threshold value, the apparatus 100 for displaying a medical image may represent that the synthesis is successful on the overlapped region by using at least one of color, a pattern, a figure, contrast, and a numerical value. In the case where the synthesis accuracy of the region in which the first image overlaps the second image is less than the threshold value, the apparatus 100 for displaying a medical image may represent that the synthesis is not successful on the overlapped region by using at least one of color, a pattern, a figure, contrast, and a numerical value.

A method of displaying the information about the synthesis accuracy in the apparatus 100 for displaying a medical image is described below with reference to FIGS. 12 to 17.

The apparatus 100 for displaying a medical image may further display a color map that maps a plurality of colors to digitized values of the synthesis accuracy. The apparatus 100 for displaying a medical image may select a color corresponding to the synthesis accuracy of the synthesis image from among a plurality of colors based on the color map, and apply the selected color to the region in which the first image overlaps the second image.

A user who uses the apparatus 100 for displaying a medical image according to an embodiment may determine to manually synthesize images for an overlapped region having low synthesis accuracy by receiving information about the synthesis accuracy of the synthesis image. The manually synthesizing of the images denotes determining overlapped regions within the images based on a user input, and synthesizing the images so that the determined overlapped regions may overlap each other.

Also, a user who uses the apparatus 100 for displaying a medical image according to an embodiment may easily recognize an overlapped region having low synthesis accuracy by receiving the information about the synthesis accuracy of the synthesis image. Therefore, the user may raise accuracy of a diagnosis or treatment of a disease by considering that the overlapped region having low synthesis accuracy may be distorted and reading the synthesis image.

Meanwhile, the apparatus 100 for displaying a medical image may further display a value of the width of a region in which the first image overlaps the second image on the region in which the first image overlaps the second image.

In the case where the width of a region in which each region overlaps another region is determined as a constant predetermined value when the apparatus for obtaining a medical image obtains a plurality of images of a plurality of regions of an object, it may be determined that the synthesis accuracy of a synthesis image deteriorates when a difference between a value of the width of a region in which the first image overlaps the second image and the predetermined value is large. Therefore, a user who uses the apparatus 100 for displaying a medical image may easily determine the synthesis accuracy of the synthesis image based on the width of the region in which the first image overlaps the second image.

A method of generating a synthesis image in the apparatus 100 for displaying a medical image according to an embodiment is described below with reference to FIGS. 7A to 7C.

Figure 7A:
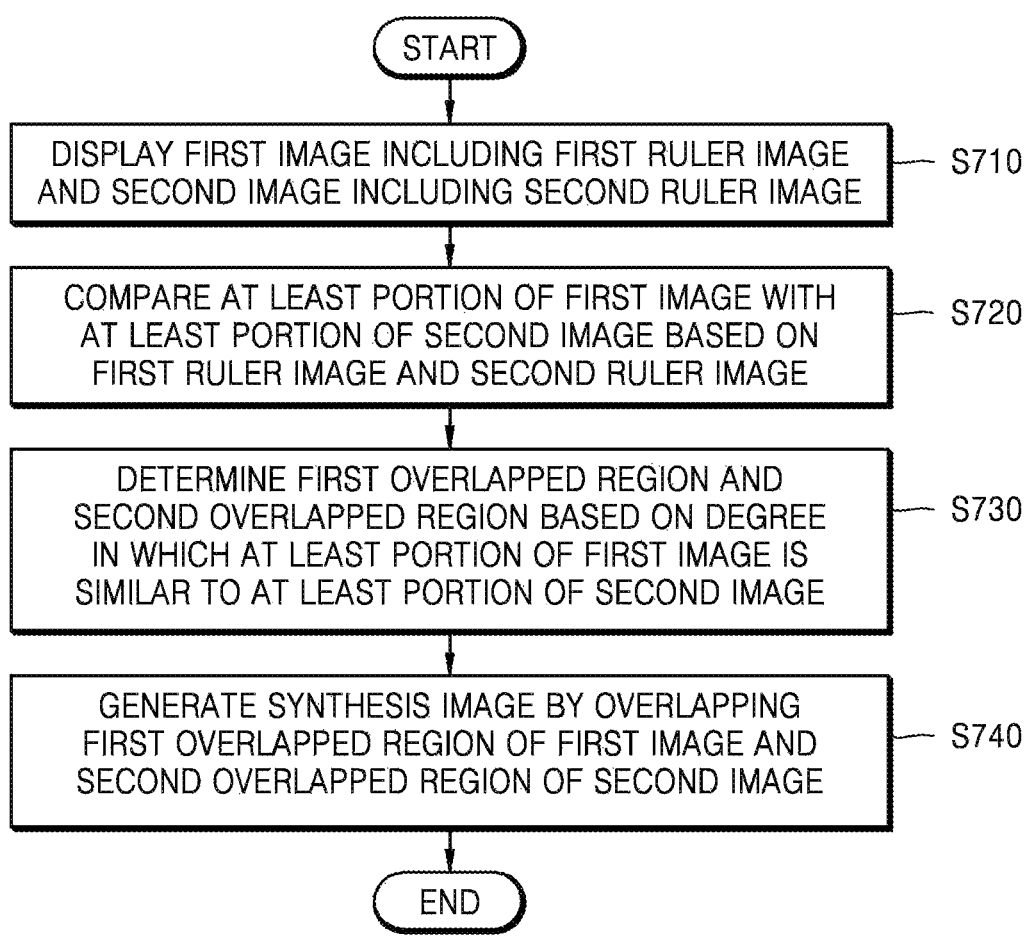
FIG. 7A is a flowchart illustrating a method of generating a synthesis image in an apparatus for displaying a medical image, according to an embodiment.

FIG. 7A is a flowchart illustrating a method of generating a synthesis image in an apparatus for displaying a medical image according to an embodiment.

In operation S710, the apparatus 100 for displaying a medical image may display the first image including the first ruler image and the second image including the second ruler image.

The first ruler image and the second ruler image may represent information about the locations of the first image and the second image, respectively. For example, the first ruler image may represent information about a distance from a reference point to a portion of an object displayed on the first image, and the second ruler image may represent information about a distance from the reference point to a portion of the object displayed on the second image. The ruler image included in each image may be a captured image of a lead ruler put beside an object, or a virtual ruler image generated based on information obtained from the apparatus for obtaining a medical image.

The ruler image included in the image may represent values between a distance from the reference point to one side of the image and a distance from the reference point to the other side of the image. The ruler image included in the image may include gradations representing, with a predetermined interval, the values between a distance from the reference point to one side of the image and a distance from the reference point to the other side of the image.

For example, in the case where the first image and the second image are X-ray images, a distance from the reference point to one side of the image and a distance from the reference point to the other side of the image may correspond to a distance from the reference point to one side of the X-ray detector of a location for obtaining the relevant image and a distance from the reference point to the other side of the X-ray detector of a location for obtaining the relevant image, respectively.

Figure 7B:
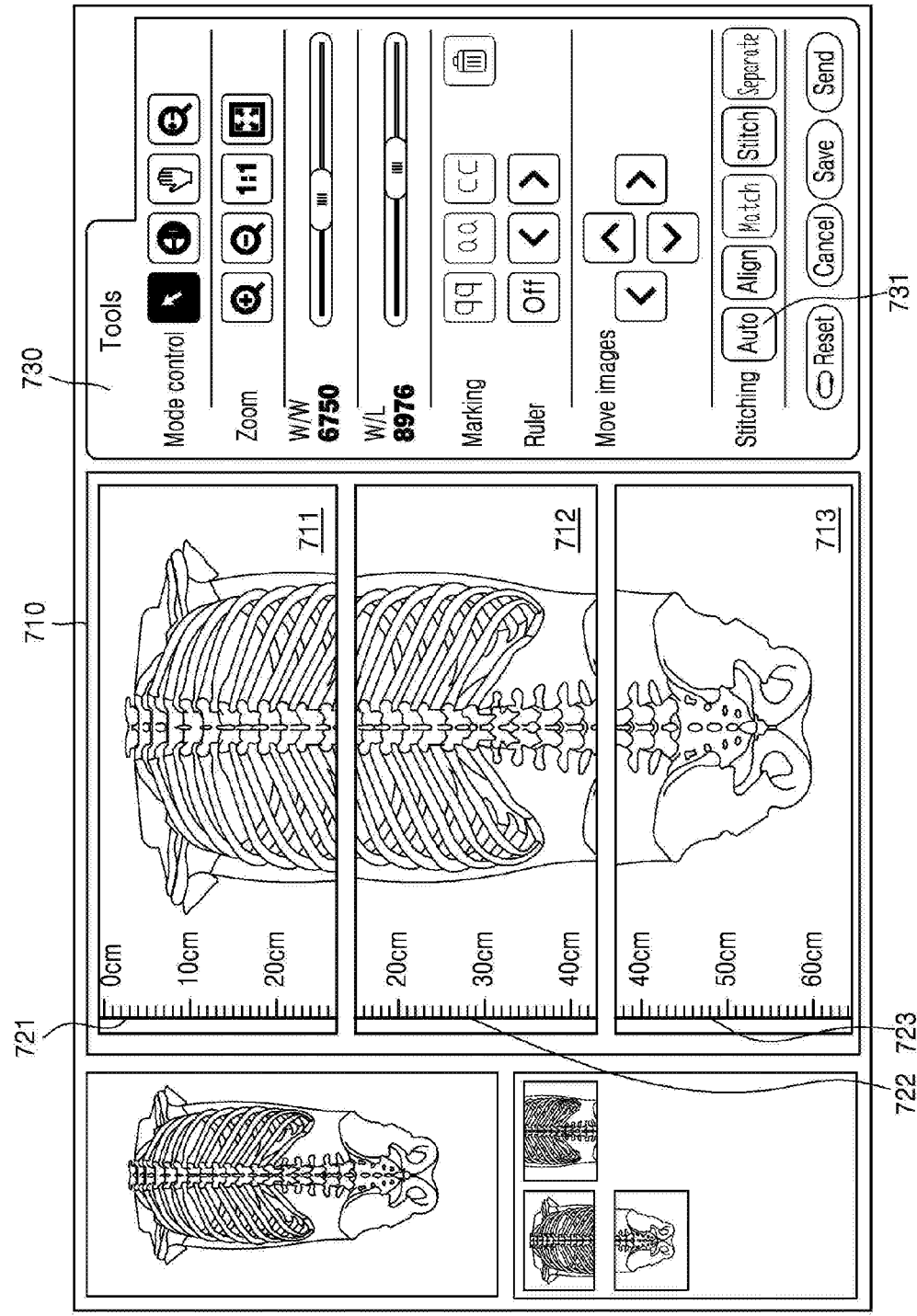
FIGS. 7B and 7C are diagrams for explaining a method of generating a synthesis image in an apparatus for displaying a medical image, according to an embodiment.

FIG. 7B illustrates an example of a screen displayed by the apparatus 100 for displaying a medical image.

The apparatus 100 for displaying a medical image may display a plurality of images 711, 712, and 713 in which ruler images 721, 722, and 723 are displayed, respectively, in a predetermined region 710 of a screen. The apparatus 100 for displaying a medical image may display a tool bar 730 for controlling the first image 711, the second image 712, and the third image 713 in a region different from the region 710. The tool bar 730 is an interface provided to a user, and the user may input a user input via the tool bar 730.

The apparatus 100 for displaying a medical image may provide an auto stitching function to the user. When receiving a user input that selects an icon 731 corresponding to the auto stitching function, the apparatus 100 for displaying a medical image may automatically synthesize the first image 711, the second image 712, and the third image 713.

In operation S720, the apparatus 100 for displaying a medical image may compare at least a portion of the first image with at least a portion of the second image based on the first ruler image and the second ruler image.

When receiving a user input that selects the icon 731 corresponding to the auto stitching function, the apparatus 100 for displaying a medical image may automatically synthesize the first image and the second image.

The apparatus 100 for displaying a medical image may compare images, and generate a synthesis image of the first image and the second image based on a result of the comparison. The apparatus 100 for displaying a medical image may determine overlapped regions whose images are captured images of the same portion of an object by comparing the images.

In this case, the apparatus 100 for displaying a medical image may compare neighboring regions of points having the same value on the first ruler image and the second ruler image instead of comparing the entire region of the first image with the entire region of the second image. Therefore, the apparatus 100 for displaying a medical image may reduce a load of an amount of calculation when comparing the entire region of the first image with the entire region of the second image, and raise a processing speed.

In operation S730, the apparatus 100 for displaying a medical image may determine the first overlapped region and the second overlapped region based on a similarity between at least a portion of the first image and at least a portion of the second image.

The apparatus 100 for displaying a medical image may calculate a similarity between at least a portion of the first image and at least a portion of the second image by comparing the first image with the second image. The apparatus 100 for displaying a medical image may determine a region of the first image that has a highest similarity and a region of the second image that has a highest similarity as the first overlapped region and the second overlapped region, respectively.

In operation S740, the apparatus 100 for displaying a medical image may generate a synthesis image by overlapping the first overlapped region of the first image and the second overlapped region of the second image.

Figure 7C:
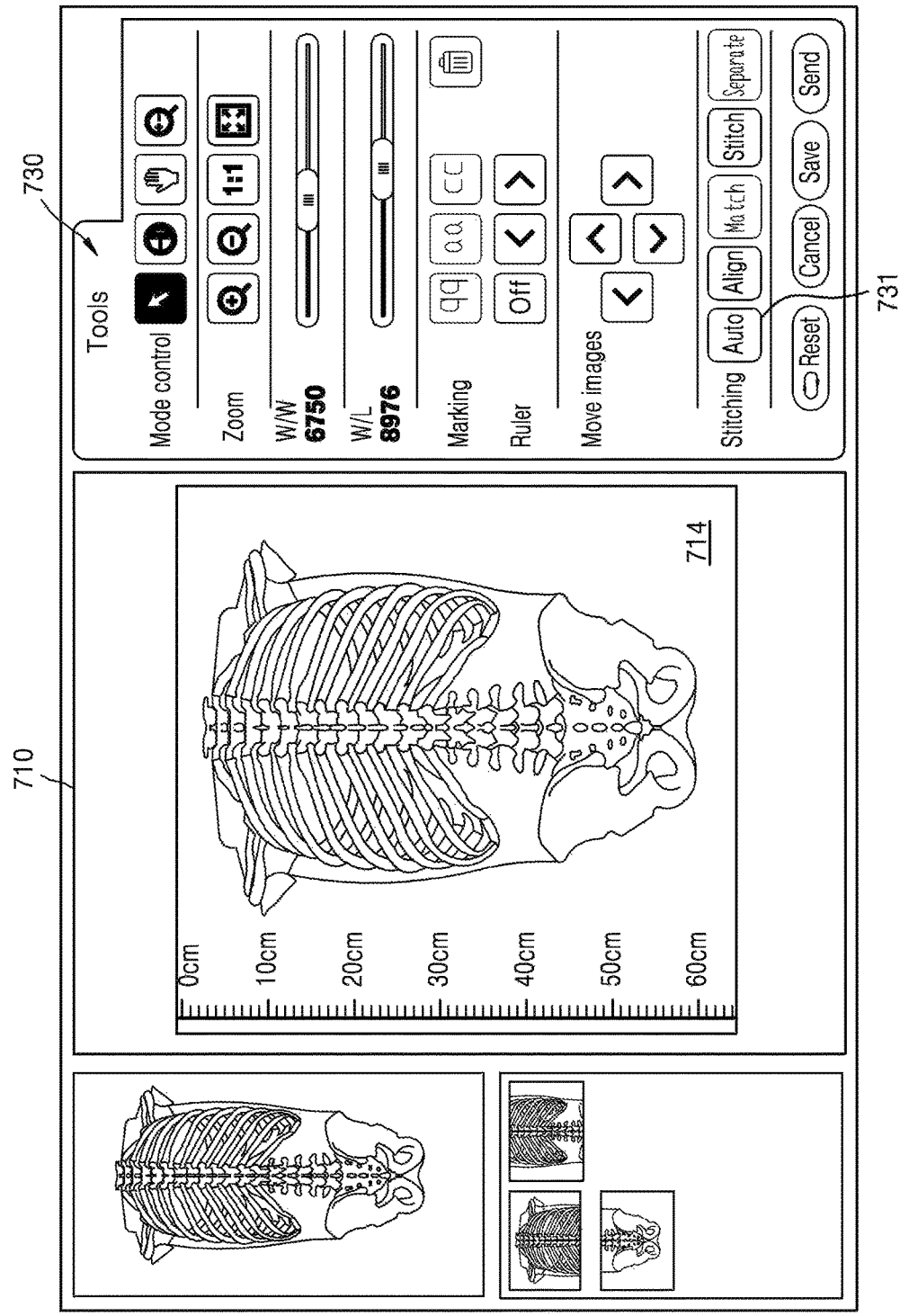

FIG. 7C illustrates an example of a screen that displays a synthesis image 714 in which the first image 711, the second image 712, and the third image 713 are synthesized.

The apparatus 100 for displaying a medical image according to an embodiment may generate a synthesis image by overlapping the first image and the second image based on only the first ruler image and the second ruler image without performing operations S720 and S730. The apparatus 100 for displaying a medical image may synthesize the first image and the second image by overlapping points having the same value on the first ruler image displayed on the first image and the second ruler image displayed on the second image.

However, a time difference may occur until the second image is obtained after the first image is obtained. In the case where a user moves during the time difference, the locations of the user when the first image is obtained and when the second image is obtained may change. Therefore, in the case where the apparatus 100 for displaying a medical image generates a synthesis image based on only the ruler image, the first image and the second image may not be combined seamlessly.

Therefore, the apparatus 100 for displaying a medical image according to an embodiment may more precisely generate a synthesis image by combining the first image with the second image based on a result of comparing at least a portion of the first image with at least a portion of the second image.

To accurately diagnose or treat a disease by using a synthesis image, the synthesis image in which a plurality of images are accurately synthesized without distortion should be provided to a user. Also, the user who receives the synthesis image should be able to intuitively determine whether the synthesis image without distortion is provided.

However, in the case where the apparatus 100 for displaying a medical image performs auto stitching, synthesis accuracy (that is, a degree in which portions of an object represented by regions in which a plurality of images overlap in order to generate a synthesis image coincide with each other) of the synthesis image 431 may reduce due to an error of the apparatus, an error of an image analysis result, or the movement of an object.

Therefore, the apparatus 100 for displaying a medical image according to an embodiment may obtain synthesis accuracy with respect to the synthesis image, and provide the synthesis accuracy to the user.

A method of obtaining information about synthesis accuracy in the apparatus 100 for displaying a medical image is described below with reference to FIGS. 8 to 11.

Figure 8:
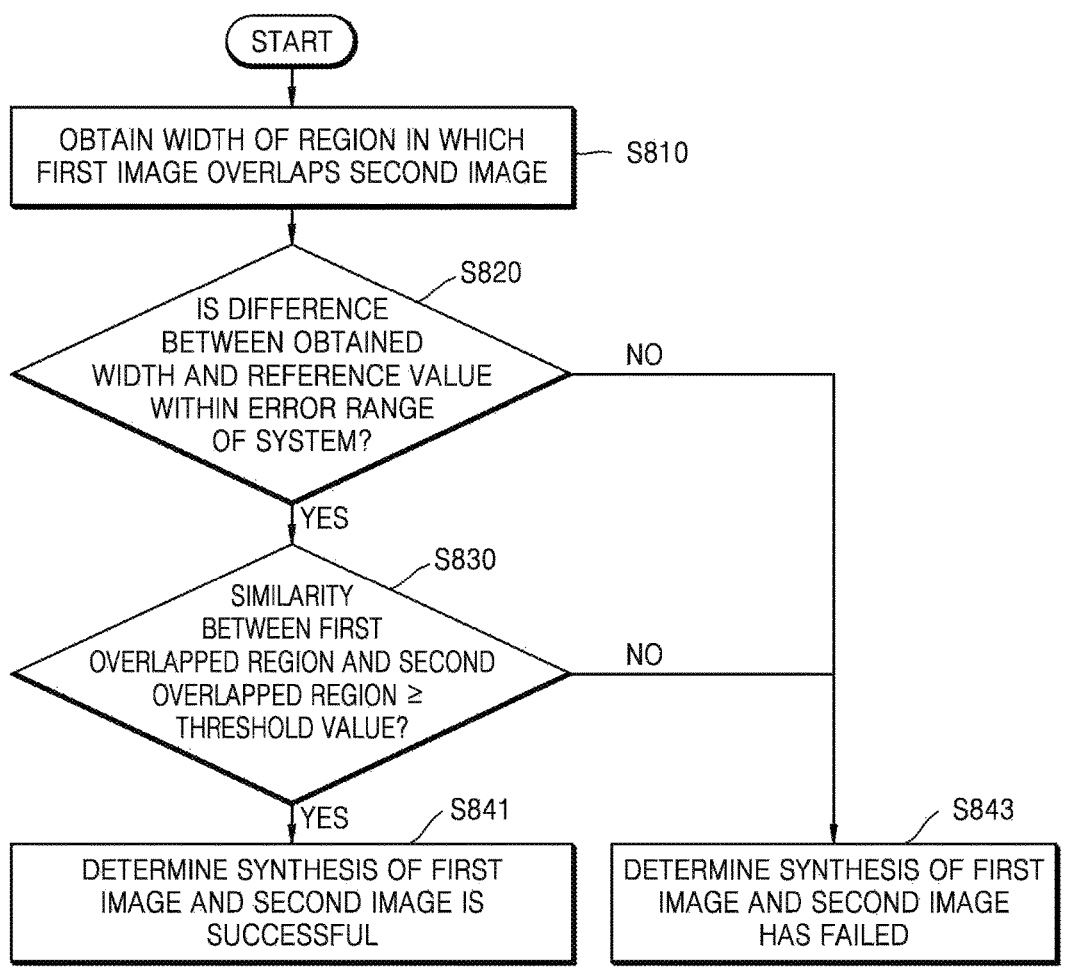
FIG. 8 is a flowchart illustrating a method of obtaining synthesis accuracy in an apparatus for displaying a medical image, according to an embodiment.

FIG. 8 is a flowchart illustrating a method of obtaining synthesis accuracy in an apparatus for displaying a medical image according to an embodiment.

In operation S810, when a synthesis image is generated from the first image and the second image, the apparatus 100 for displaying a medical image may obtain the width of a region in which the first image overlaps the second image in order to generate the synthesis image. The width of the region in which the first image overlaps the second image in order to generate the synthesis image may correspond to the width of the first overlapped region or the second overlapped region determined in operation S730 of FIG. 7A.

In operation S820, the apparatus 100 for displaying a medical image may determine whether a difference between the width of the overlapped region obtained in operation S810 and a reference value is within an error range of the system. The error range of the system may be a value determined in advance as a default value, or a value determined based on a user input.

The apparatus 100 for displaying a medical image may determine the reference value based on location information of images. The apparatus 100 for displaying a medical image may determine the reference value based on information about a distance from a reference point to a portion of an object displayed on an image.

The apparatus 100 for displaying a medical image may determine the reference value based on a ruler image included in an image. The apparatus 100 for displaying a medical image may obtain a first distance value displayed on one side of the first image included in the first overlapped region and a second distance value displayed on the other side of the second image included in the second overlapped region, and determine a difference between the first distance value and the second distance value as the reference value.

Alternatively, the apparatus 100 for displaying a medical image may determine the reference value based on information about a distance from a reference point obtained from the apparatus for obtaining a medical image to a portion of an object displayed on an image.

For example, in the case where the first image and the second image are X-ray images, the apparatus 100 for displaying a medical image may obtain information about a distance from the reference point to a portion of an object displayed on an image based on at least one of information about the location of the X-ray irradiator that obtains images, information about a rotational angle of the X-ray irradiator, information about the location of the detector, and information about the size of the detector. The apparatus 100 for displaying a medical image may determine the reference value based on the width of a region overlapped by the detector when capturing images.

Alternatively, the apparatus 100 for displaying a medical image may determine the width of a region in which each region overlaps another region as the reference value when the apparatus for obtaining a medical image obtains a plurality of images of a plurality of regions of an object. The width of the region in which each region overlaps another region may be determined in advance as a default value, or determined by a user input.

When determining a difference between the width of a region in which the first image overlaps the second image and the reference value exceeds the error range of the system, the apparatus 100 for displaying a medical image may determine that synthesis of the first image and the second image has failed (S843).

When determining a difference between the width of a region in which the first image overlaps the second image and the reference value is within the error range of the system, the apparatus 100 for displaying a medical image may compare the first overlapped region of the first image with the second overlapped region of the second image (S830). The apparatus 100 for displaying a medical image may calculate a similarity between the first overlapped region and the second overlapped region, and compare the calculated similarity with a threshold value determined in advance.

When the similarity between the first overlapped region and the second overlapped region is equal to or greater than a threshold value, the apparatus 100 for displaying a medical image may determine that the first image and the second image have been successfully synthesized (S841). When the similarity between the first overlapped region and the second overlapped region is less than the threshold value, the apparatus 100 for displaying a medical image may determine that the synthesis of the first image and the second image has failed (S843).

As illustrated in FIG. 8, the apparatus 100 for displaying a medical image may obtain information as to whether the synthesis of the first image and the second image is successful as information about synthesis accuracy.

However, an embodiment is not limited to the description illustrated in FIG. 8, and the apparatus 100 for displaying a medical image may obtain a digitized value of the synthesis accuracy as the information about the synthesis accuracy. For example, the apparatus 100 for displaying a medical image may obtain a difference value between the width of the region in which the first image overlaps the second image and the reference value as the information about the synthesis accuracy. Alternatively, the apparatus 100 for displaying a medical image may obtain a ratio in which the difference value between the width of the region in which the first image overlaps the second image and the reference value deviates from the error of the system as the information about the synthesis accuracy.

Figure 9:
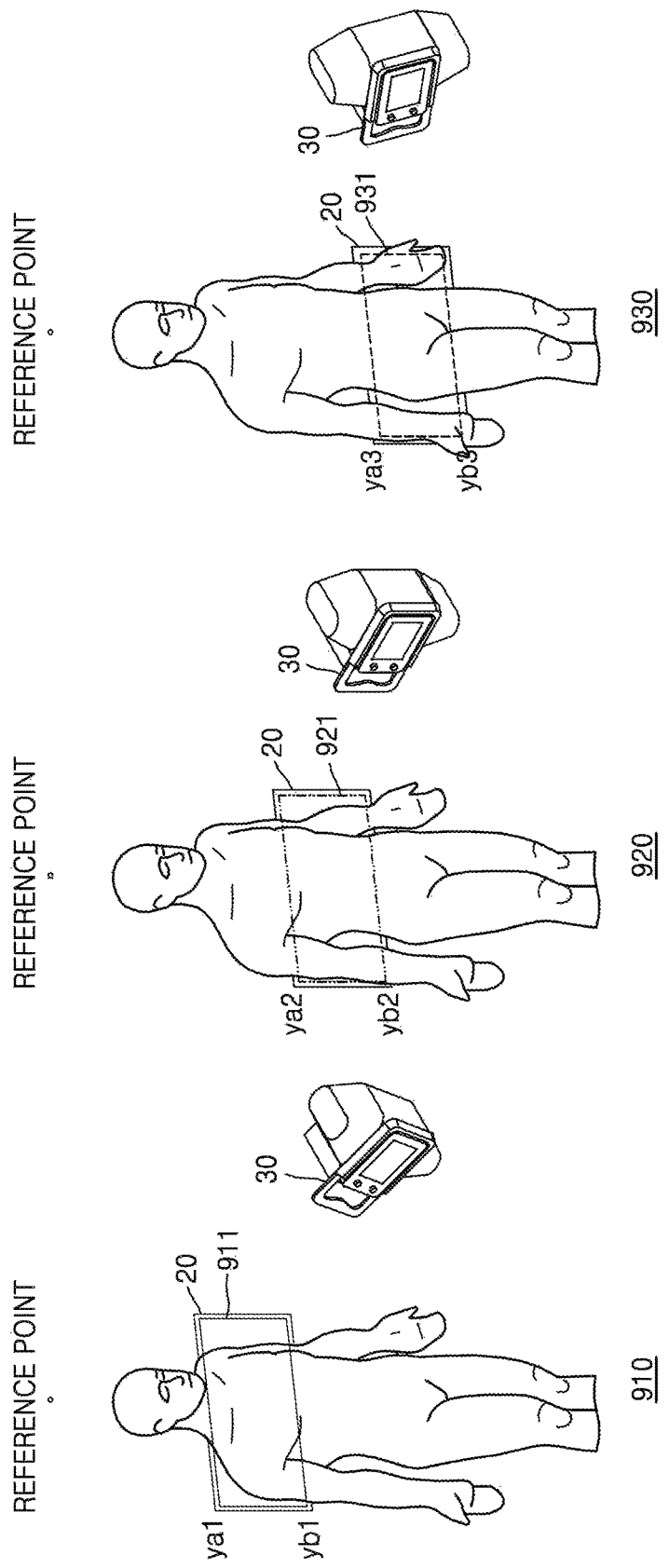
FIGS. 9 to 11 are diagrams for explaining a method of obtaining synthesis accuracy in an apparatus for displaying a medical image, according to an embodiment.
Figure 10:
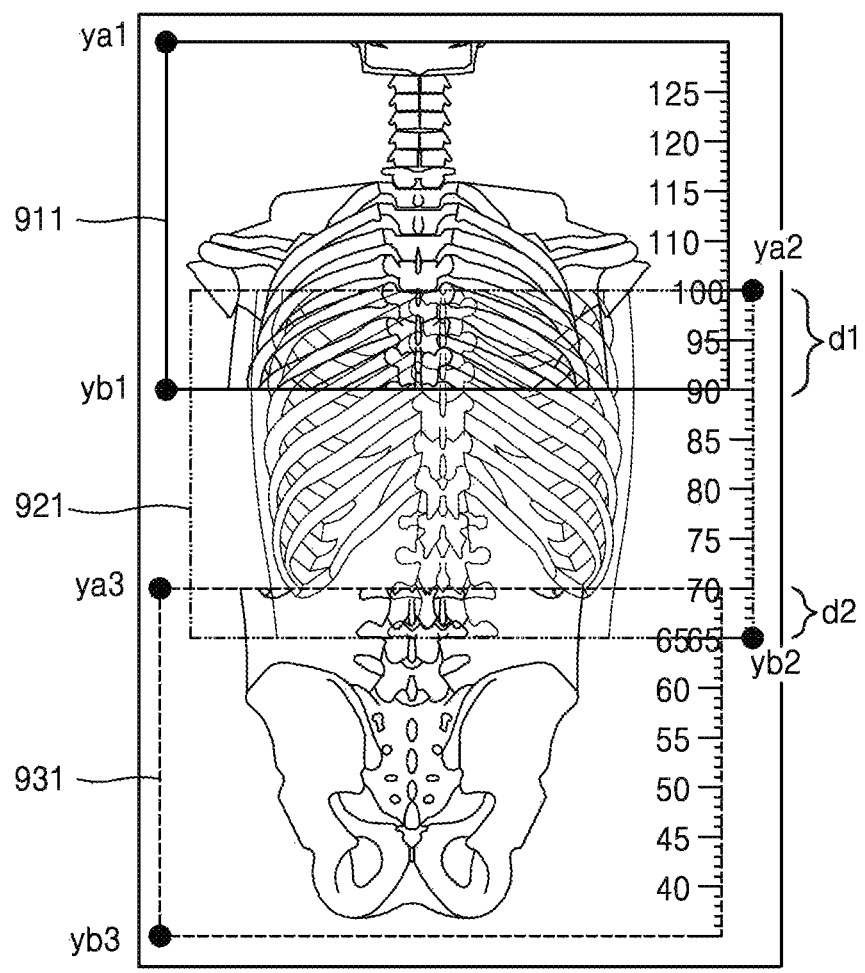
Figure 11:
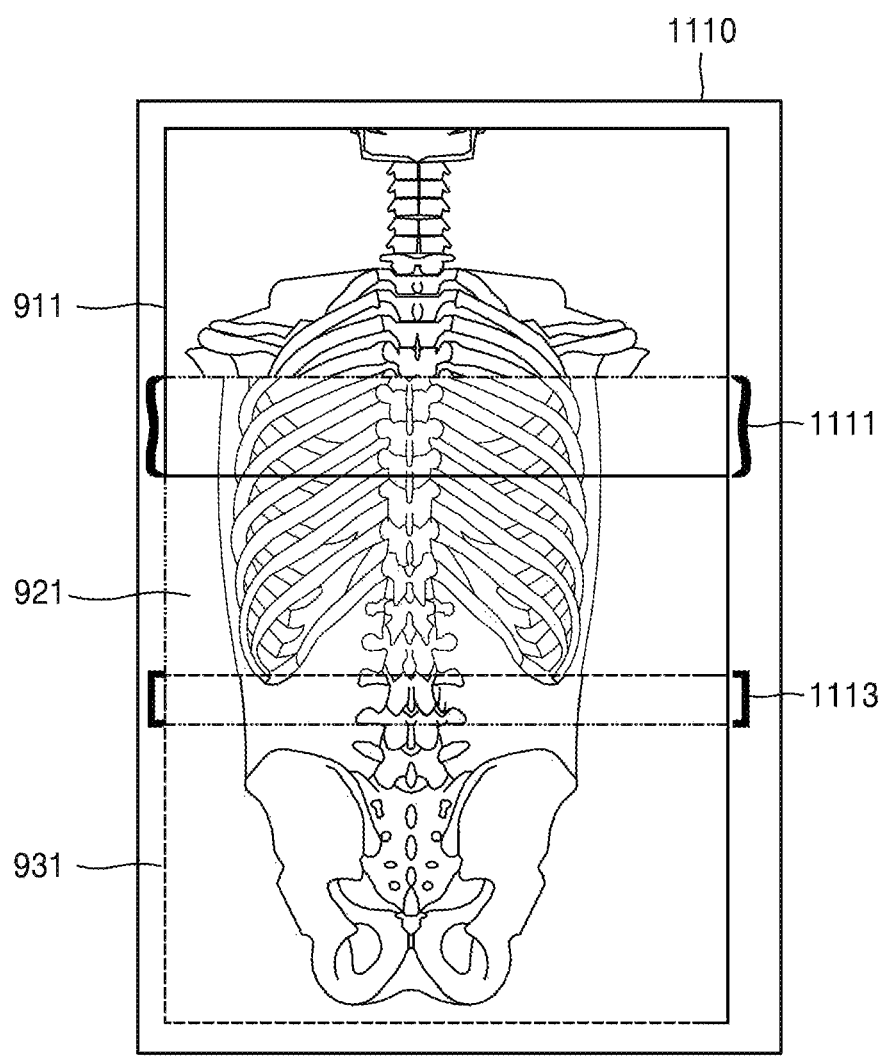

FIGS. 9 to 11 are diagrams for explaining a method of obtaining synthesis accuracy in an apparatus for displaying a medical image according to an embodiment. Though FIGS. 9 to 11 illustrate a case in which the apparatus 100 for displaying a medical image displays an X-ray image as an example, the apparatus 100 for displaying a medical image according to an embodiment is not limited to displaying an X-ray image.

As illustrated in FIG. 9, the X-ray capturing apparatus may obtain a plurality of images of a plurality of regions of an object. The X-ray capturing apparatus may divide the object into a plurality of regions along a predetermined direction, rotate the X-ray irradiator 30 by a rotational angle corresponding to each region, move the detector 20 to a location corresponding to each region, and then obtain an image of each region. To generate a synthesis image, images of respective regions of the object may be obtained so that portions of the images may overlap each other.

As illustrated in an image 910 of FIG. 9, the X-ray capturing apparatus may change the direction of an X-ray irradiated to the object by rotating the X-ray irradiator 20 in order to obtain a first image 911 of a first region of the object. As the X-ray irradiator 30 rotates, the detector 20 may move to a location corresponding to the first region in a predetermined direction. In the detector 20 that has moved to the location corresponding to the first region, a distance from a reference point to one side of the detector 20 may be ya1, and a distance from the reference point to other side of the detector 20 may be yb1.

As illustrated in an image 920 of FIG. 9, the X-ray capturing apparatus may change the direction of an X-ray irradiated to the object by rotating the X-ray irradiator 20 in order to obtain a second image 921 of a second region of the object. As the X-ray irradiator 30 rotates, the detector 20 may move to a location corresponding to the second region in a predetermined direction. In the detector 20 that has moved to the location corresponding to the second region, a distance from a reference point to one side of the detector 20 may be ya2, and a distance from the reference point to other side of the detector 20 may be yb2.

As illustrated in an image 930 of FIG. 9, the X-ray capturing apparatus may change the direction of an X-ray irradiated to the object by rotating the X-ray irradiator 20 in order to obtain a third image 931 of a third region of the object. As the X-ray irradiator 30 rotates, the detector 20 may move to a location corresponding to the third region in a predetermined direction. In the detector 20 that has moved to the location corresponding to the third region, a distance from a reference point to one side of the detector 20 may be ya3, and a distance from the reference point to other side of the detector 20 may be yb3.

As illustrated in FIG. 10, the apparatus 100 for displaying a medical image may display the plurality of images 911, 921, and 931 obtained with respect to the plurality of regions of the object. Each of the plurality of images 911, 921, and 931 may include a ruler image representing location information of the relevant image. The location information of the image may correspond to location information of the detector when the relevant image is captured.

For example, a first ruler image included in the first image 911 may represent ya1, which is a distance from the reference point to one side of the detector 20, and yb1, which is a distance from the reference point to the other side of the detector 20. A second ruler image included in the second image 921 may represent ya2, which is a distance from the reference point to one side of the detector 20, and yb2, which is a distance from the reference point to the other side of the detector 20. A third ruler image included in the third image 931 may represent ya3, which is a distance from the reference point to one side of the detector 20, and yb3, which is a distance from the reference point to the other side of the detector 20.

As illustrated in FIG. 10, the apparatus 100 for displaying a medical image may generate a synthesis image by overlapping the plurality of images 911, 921, and 931. The apparatus 100 for displaying a medical image may compare the plurality of images 911, 921, and 931 with each other, and generate the synthesis image by overlapping the plurality of images 911, 921, and 931 based on a result of the comparison.

The apparatus 100 for displaying a medical image may compare the first image 911 with the second image 921, and calculate a similarity between a portion of the first image 911 and a portion of the second image 921. The apparatus 100 for displaying a medical image may overlap a portion of the first image 911 and a portion of the second image 921 whose similarities are determined as highest. The width of a region in which the first image 911 overlaps the second image 921 may be "d1".

The apparatus 100 for displaying a medical image may compare the second image 921 with the third image 931, and calculate a similarity between a portion of the second image 921 and a portion of the third image 931. The apparatus 100 for displaying a medical image may overlap a portion of the second image 921 and a portion of the third image 931 whose similarities are determined as highest. The width of a region in which the second image 921 overlaps the third image 931 may be "d2".

The apparatus 100 for displaying a medical image may obtain information about synthesis accuracy by comparing an error of the system with a difference value between the width "d1" of the region in which the first image 911 overlaps the second image 921 and a reference value. The apparatus 100 for displaying a medical image may determine the reference value based on a ruler image included in the image. The apparatus 100 for displaying a medical image may determine the reference value based on location information of images. For example, the apparatus 100 for displaying a medical image may determine the width of an overlapped region between regions set when capturing the images as the reference value.

The apparatus 100 for displaying a medical image may determine the width of a section overlapped by the detector 20 located at a first location for capturing the first image 911 and the detector 20 located at a second location for capturing the second image 921 as the reference value. The reference value r1 may be obtained by Equation 1 below.

$$r1 = ya2 - yb1 \quad \text{Equation 1}$$

The difference value "D" between the width "d1" of the region in which the first image 911 overlaps the second image 921, and the reference value "r1" may be obtained by Equation 2 below.

$$D = |r1 - d1| = |(ya2 - yb1) - d1| \quad \text{Equation 2}$$

When an error of the medical image system including the apparatus 100 for displaying a medical image is "w", a ratio "R" in which a difference value between the width of the region in which the first image overlaps the second image and the reference value deviates from the error of the system may be obtained by Equation 3 below.

$$R(\%) = \frac{|D - w|}{w} \times 100 = \frac{||(ya2 - yb1) - d1| - w|}{w} \times 100 \quad \text{Equation 3}$$

The apparatus 100 for displaying a medical image may obtain the ratio "R" in which a difference value between the width of the region in which the first image 911 overlaps the second image 921 and the reference value deviates from the error of the system as information about synthesis accuracy. The apparatus 100 for displaying a medical image may also obtain information about synthesis accuracy by using the above-described method with respect to a region in which the second image 921 overlaps the third image 931. Repeated description thereof is omitted.

As illustrated in FIG. 11, the apparatus 100 for displaying a medical image may generate a synthesis image 1110 by synthesizing the plurality of images 911, 921, and 931 obtained from the apparatus for obtaining a medical image, and display overlapped sections 1111 and 1113 in which the plurality of images 911, 921, and 931 configuring the synthesis image 1110 overlap each other on the synthesis image 1110. Also, the apparatus 100 for displaying a medical image may display the synthesis accuracy of the synthesis image 1110 on the synthesis image 1110. Information about the synthesis accuracy may be displayed on the synthesis image by using various methods that use at least one of a color, a pattern, a figure, contrast, and a numerical value. The apparatus 100 for displaying a medical image may display the information about the synthesis accuracy according to a selected method based on a user input.

A method of displaying information about synthesis accuracy on a synthesis image in the apparatus 100 for displaying a medical image according to an embodiment is described below with reference to FIGS. 12 to 17.

Figure 12:
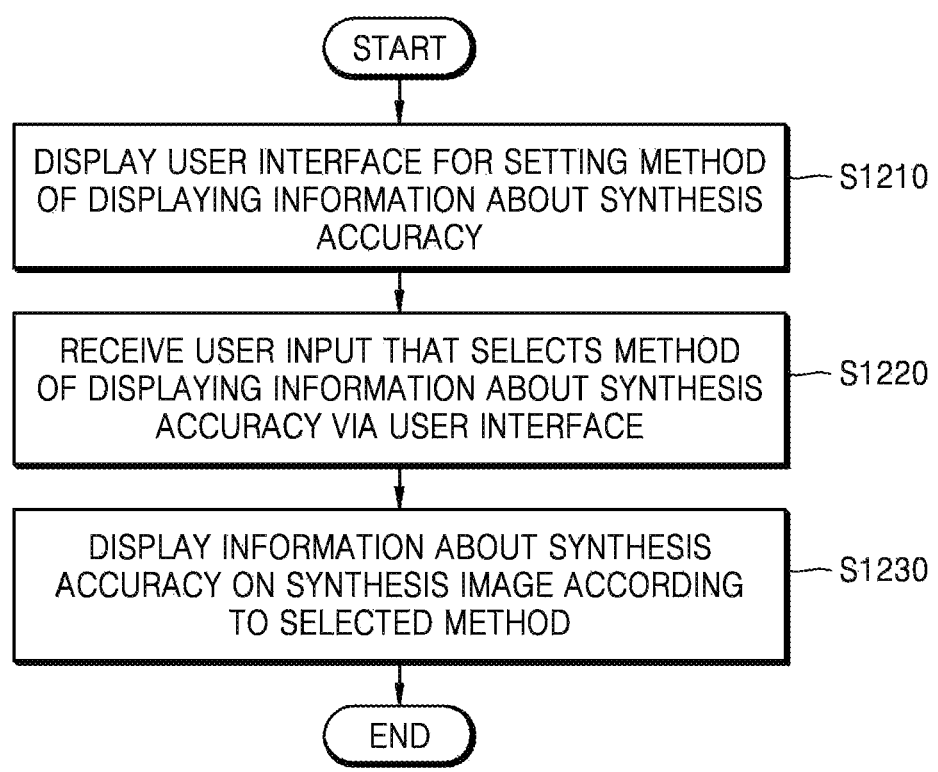
FIG. 12 is a flowchart illustrating a method of selecting a method of displaying information about synthesis accuracy based on a user input in an apparatus for displaying a medical image, according to an embodiment.

FIG. 12 is a flowchart illustrating a method of selecting a method of displaying information about synthesis accuracy based on a user input in an apparatus for displaying a medical image according to an embodiment.

In operation S1210, the apparatus 100 for displaying a medical image may display a user interface for setting a method of displaying the information about the synthesis accuracy. The apparatus 100 for displaying a medical image may display a user interface for determining a form from among a color, a pattern, a figure, contrast, and a numerical value in which the information about the synthesis accuracy is displayed.

Figure 13:
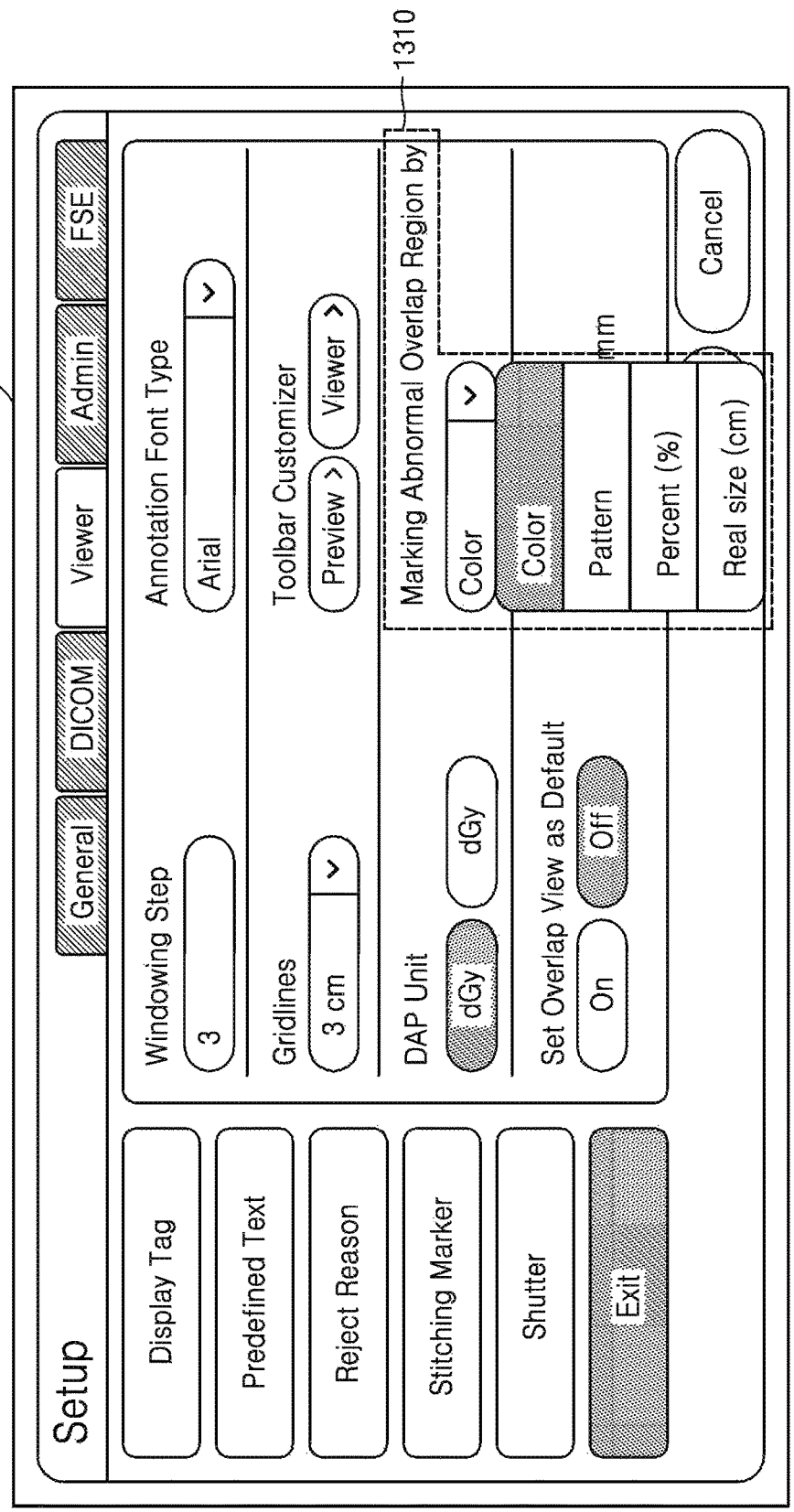
FIG. 13 is a diagram illustrating an example of a user interface displayed by an apparatus for displaying a medical image in order to receive a user input selecting a method of displaying information about synthesis accuracy, according to an embodiment.

FIG. 13 is a diagram illustrating an example of a user interface displayed by an apparatus for displaying a medical image in order to receive a user input selecting a method of displaying information about synthesis accuracy according to an embodiment.

The apparatus 100 for displaying a medical image may display a user interface 1300 related to a medical image. The user interface 1300 related to a medical image may include at least one of a user interface for setting a parameter related to a medical image, a user interface for controlling an external device or a server connected with the apparatus 100 for displaying a medical image, and a user interface for displaying information about a medical image.

As illustrated in FIG. 13, the user interface 1300 related to the medical image may include a user interface 1310 for selecting a method of displaying information about synthesis accuracy. The user interface 1310 may include a menu that lists a method of displaying the synthesis accuracy by using various colors, a method of displaying the synthesis accuracy by using various patterns, a method of displaying the synthesis accuracy by using a digitized value (%) of the synthesis accuracy, and a method of displaying the synthesis accuracy by using the width of an overlapped region.

In operation S1220, the apparatus 100 for displaying a medical image may receive a user input that selects a method of displaying the information about the synthesis accuracy via the user interface.

The apparatus 100 for displaying a medical image may receive a user input that selects at least one method from the menu that lists the methods of displaying the information about the synthesis accuracy.

In operation S1230, the apparatus 100 for displaying a medical image may display the information about the synthesis accuracy on the synthesis image according to the method selected in operation S1220.

FIGS. 14 to 17 are diagrams illustrating an example of a synthesis image including information about synthesis accuracy, displayed by an apparatus for displaying a medical image according to an embodiment.

Figure 15:
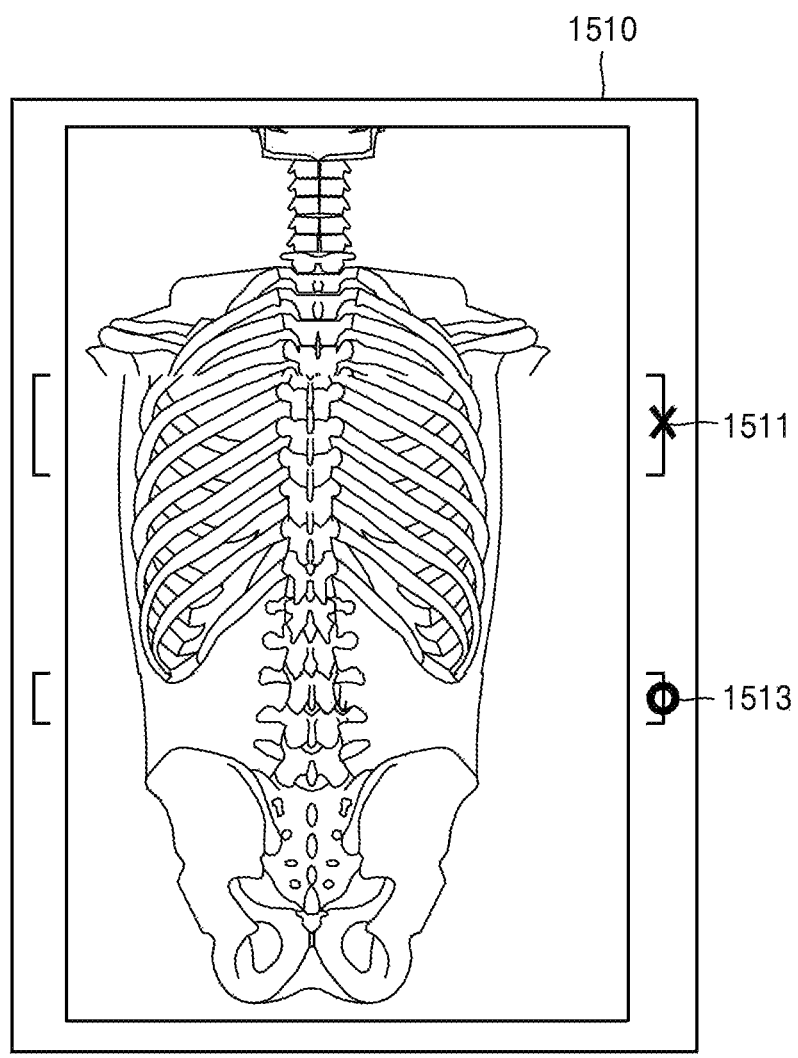

As illustrated in FIG. 15, the apparatus 100 for displaying a medical image may display the information about the synthesis accuracy by using markers 1411 and 1413 displayed on an overlapped region of a synthesis image 1410.

The apparatus 100 for displaying a medical image may display a marker having color, a pattern, a thickness, or contrast corresponding to the synthesis accuracy of each overlapped region on the overlapped region.

The apparatus 100 for displaying a medical image may indicate an overlapped section in which images overlap each other based on the length of the marker, and indicate information about the synthesis accuracy of images based on at least one of color, a pattern, a thickness, and contrast of the marker.

For example, the apparatus 100 for displaying a medical image may display the marker 1411 including color corresponding to the synthesis accuracy of the first image and the second image on an overlapped region of the first image and the second image. The apparatus 100 for displaying a medical image may display the marker 1413 including color corresponding to the synthesis accuracy of the second image and the third image on an overlapped region of the second image and the third image.

The apparatus 100 for displaying a medical image may further display a color map 1415 that maps a plurality of colors to digitized values of the synthesis accuracy. The apparatus 100 for displaying a medical image may select colors corresponding to the synthesis accuracy of a synthesis image from among the plurality of colors based on the color map, and respectively apply the selected colors to markers on a region in which the first image overlaps the second image.

Figure 16:
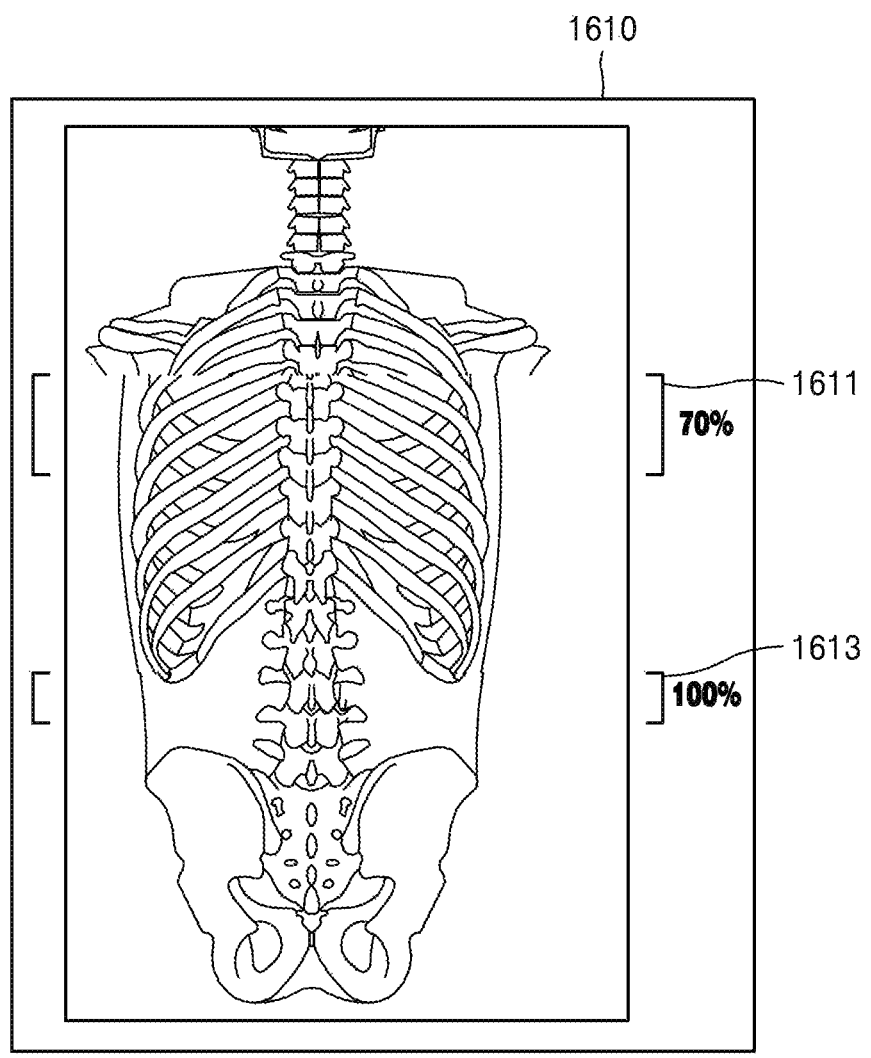

As illustrated in FIG. 16, the apparatus 100 for displaying a medical image may display the information about the synthesis accuracy on an overlapped region of a synthesis image 1510 by using FIGS. 1511 and 1513.

The apparatus 100 for displaying a medical image may display a figure corresponding to the synthesis accuracy of each overlapped region on the overlapped region.

For example, the apparatus 100 for displaying a medical image may display the FIG. 1511 corresponding to the synthesis accuracy of the first image and the second image on the overlapped region of the first image and the second image. The apparatus 100 for displaying a medical image may display the FIG. 1513 corresponding to the synthesis accuracy of the second image and the third image on the overlapped region of the second image and the third image. As illustrated in FIG. 16, when determining that synthesis of images is successful, the apparatus 100 for displaying a medical image may display a figure "0" on an overlapped region. When determining that synthesis of images has failed, the apparatus 100 for displaying a medical image may display a figure "X" on the overlapped region.

Figure 17:
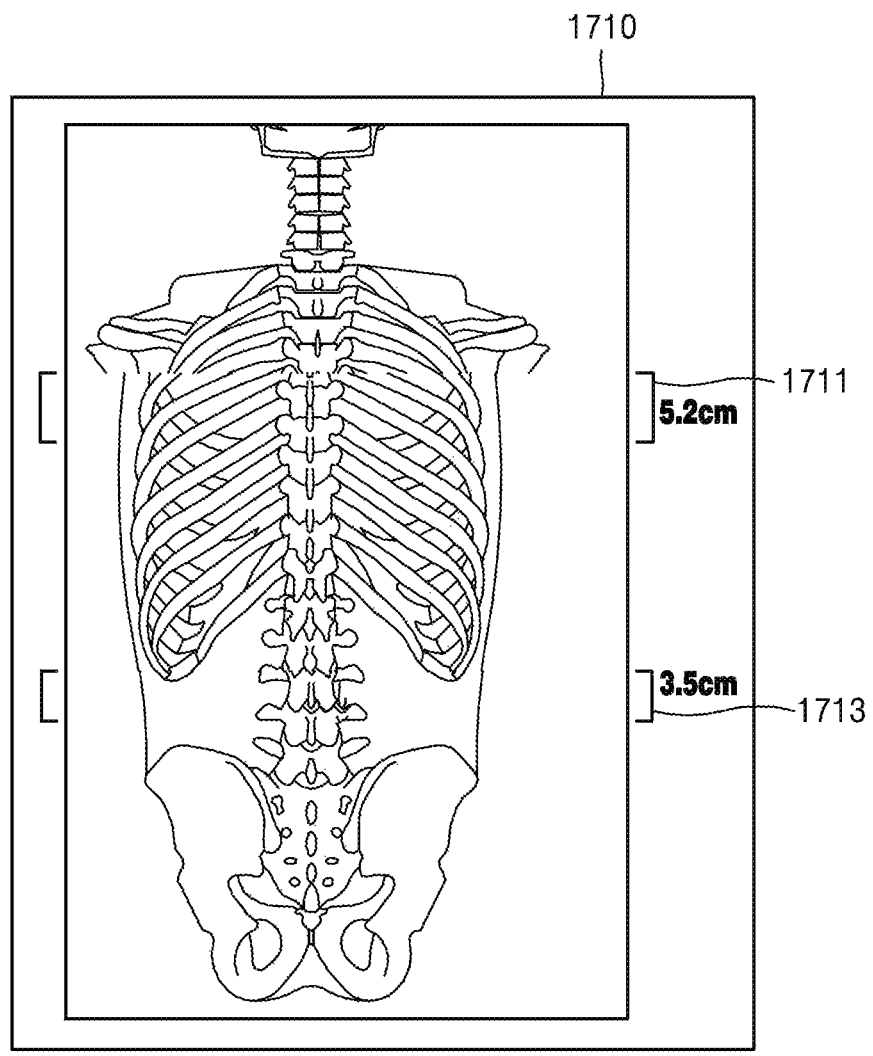
FIG. 17 is a diagram illustrating an example of a synthesis image representing a width of a region in which a plurality of images overlap, displayed by an apparatus for displaying a medical image, according to an embodiment.

Also, as illustrated in FIG. 17, the apparatus 100 for displaying a medical image may display synthesis accuracy values 1611 and 1613 on an overlapped region of a synthesis image 1610. The apparatus 100 for displaying a medical image may display a synthesis accuracy value of each overlapped region on the overlapped region. For example, a value of the synthesis accuracy may be a difference value between the width of a region in which images overlap each other and a reference value, a ratio in which the difference value between the width of a region in which images overlap each other and the reference value deviates from an error of the system, or a similarity between a first overlapped region of the first image and a second overlapped region of the second image.

The apparatus 100 for displaying a medical image may display the synthesis accuracy value 1611 of the first image and the second image on an overlapped region of the first image and the second image. The apparatus 100 for displaying a medical image may display the synthesis accuracy value 1613 of the second image and the third image on an overlapped region of the second image and the third image.

For example, the apparatus 100 for displaying a medical image may calculate a ratio in which a difference value between the width of a region in which images overlap each other and a reference value deviates from the error of the system within a synthesis image as a synthesis accuracy value. When a ratio in which a difference value between the width of a region in which the first image overlaps the second image and the reference value deviates from the error of the system approaches about 100%, the apparatus 100 for displaying a medical image may determine that the synthesis accuracy of the first image and the second image is high.

Figure 19:
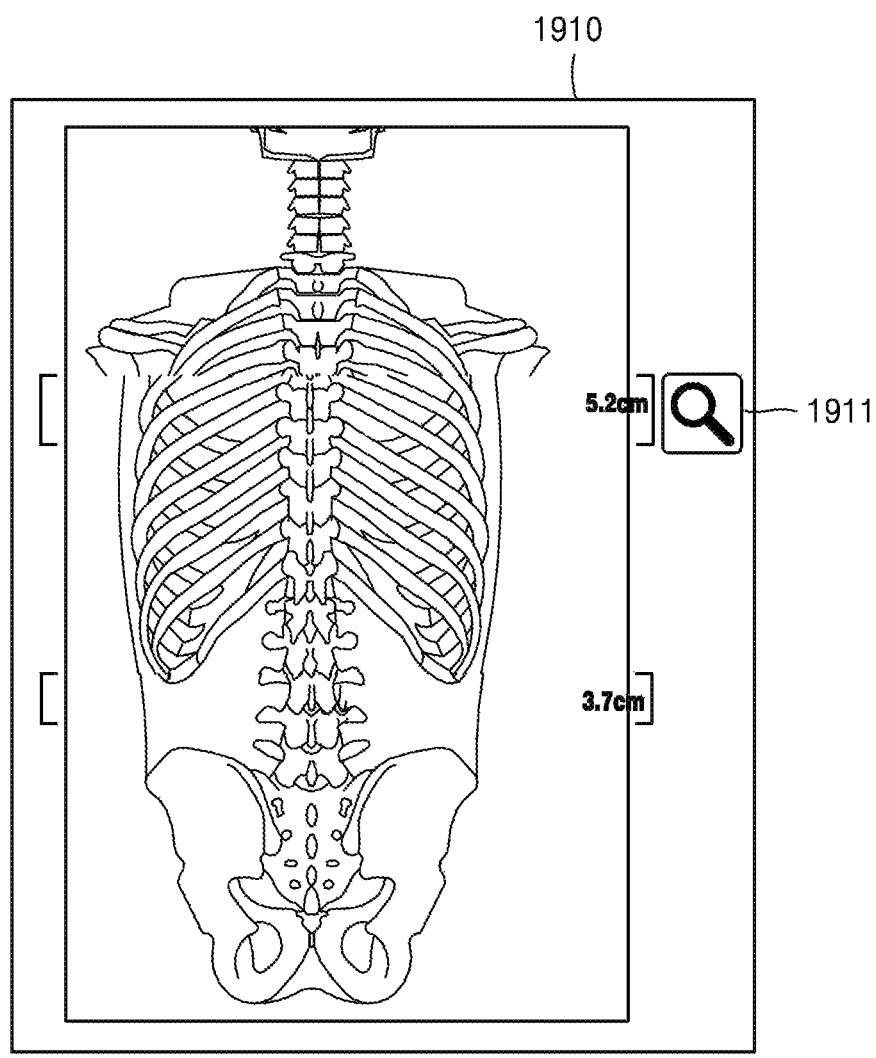
FIGS. 19 to 21 are diagrams illustrating an example of a synthesis image and a user interface displayed by an apparatus for displaying a medical image that operates in a mode for observing an overlapped region, according to an embodiment.

Meanwhile, as illustrated in FIG. 19, the apparatus 100 for displaying a medical image may display values 1711 and 1713 of the width of an overlapped region on the overlapped region of a synthesis image 1710.

For example, the apparatus 100 for displaying a medical image may display the value 1711 of the width of a region in which the first image overlaps the second image on an overlapped region of the first image and the second image. The apparatus 100 for displaying a medical image may display the value 1713 of the width of a region in which the second image overlaps the third image on an overlapped region of the second image and the third image.

When the apparatus for obtaining a medical image obtains a plurality of images of a plurality of regions of an object, the width of a region in which each region overlaps another region may be determined as a constant predetermined value. When a difference between a value of the width of a region in which the first image overlaps the second image and a predetermined value is large, a user may determine that the synthesis accuracy of a synthesis image reduces. The apparatus 100 for displaying a medical image may provide the width of the region in which the first image overlaps the second image as information about synthesis accuracy.

Meanwhile, to determine whether synthesis of a plurality of images has been accurately performed, a user may intend to observe an overlapped region in which the plurality of images overlap each other within a synthesis image in more detail. Therefore, the apparatus 100 for displaying a medical image according to an embodiment may provide a display mode for observing an overlapped region.

Figure 18:
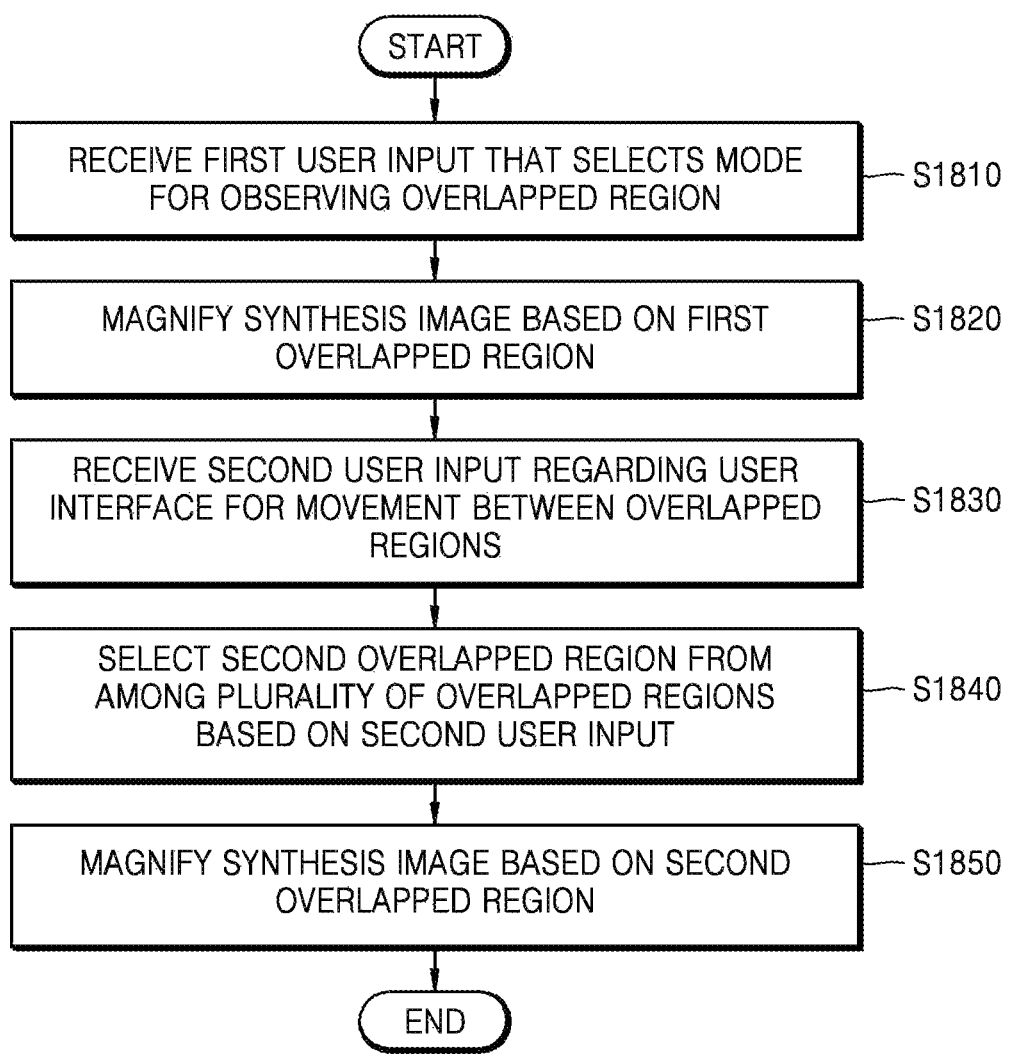
FIG. 18 is a flowchart illustrating a method of operating an apparatus for displaying a medical image under a mode for observing an overlapped region in which a plurality of images overlap, according to an embodiment.

FIG. 18 is a flowchart illustrating a method of operating an apparatus for displaying a medical image under a mode for observing an overlapped region in which a plurality of images overlap according to an embodiment.

In operation S1810, the apparatus 100 for displaying a medical image may receive a first user input that selects the display mode for observing a plurality of overlapped regions in which a plurality of images overlap each other in order to generate a synthesis image.

Figure 14:
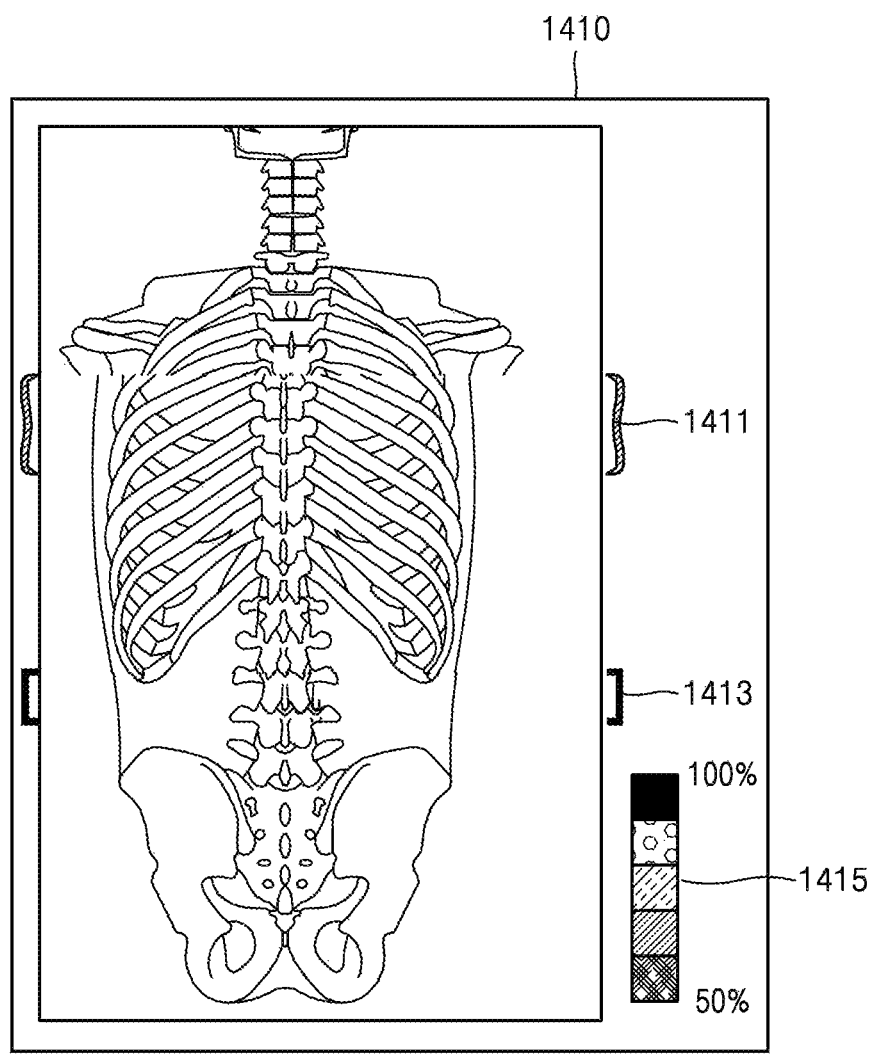
FIGS. 14 to 16 are diagrams illustrating an example of a synthesis image including information about synthesis accuracy, displayed by an apparatus for displaying a medical image, according to an embodiment.

As illustrated in FIG. 14, the apparatus 100 for displaying a medical image may display an icon 1911 for executing the mode for observing an overlapped region and a synthesis image 1910 together. When receiving a user input that selects the icon 1911, the apparatus 100 for displaying a medical image may execute the display mode for observing an overlapped region.

In operation S1820, when the display mode for observing an overlapped region is executed, the apparatus 100 for displaying a medical image may magnify the synthesis image based on a first overlapped region from among a plurality of overlapped regions of the synthesis image.

Figure 20:
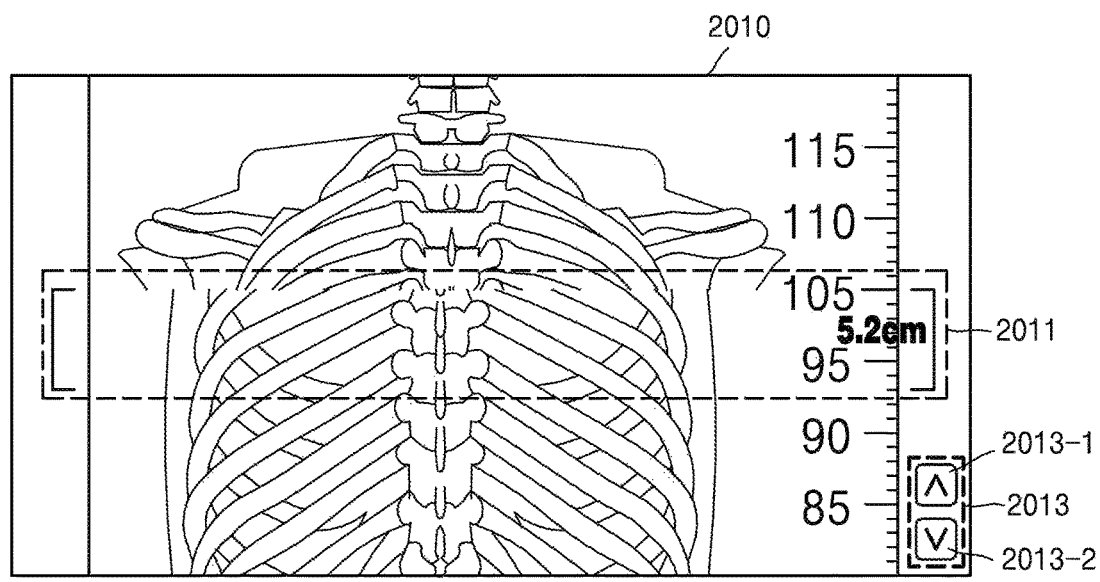

As illustrated in FIG. 20, the apparatus 100 for displaying a medical image may display a synthesis image 2010 magnified based on a first overlapped region 2011 from among a plurality of overlapped regions. The apparatus 100 for displaying a medical image may display a user interface 2013 for moving to another overlapped region on the synthesis image 2010.

In operation S1830, the apparatus 100 for displaying a medical image may receive a second user input for movement between the plurality of overlapped regions.

For example, as illustrated in FIG. 20, the apparatus 100 for displaying a medical image may receive a user input regarding a user interface 2013 for moving to another overlapped region.

In operation S1840, the apparatus 100 for displaying a medical image may select a second overlapped region from among the plurality of overlapped regions based on the second user input. In operation S1850, the apparatus 100 for displaying a medical image may magnify a synthesis image based on the second overlapped region.

Figure 21:
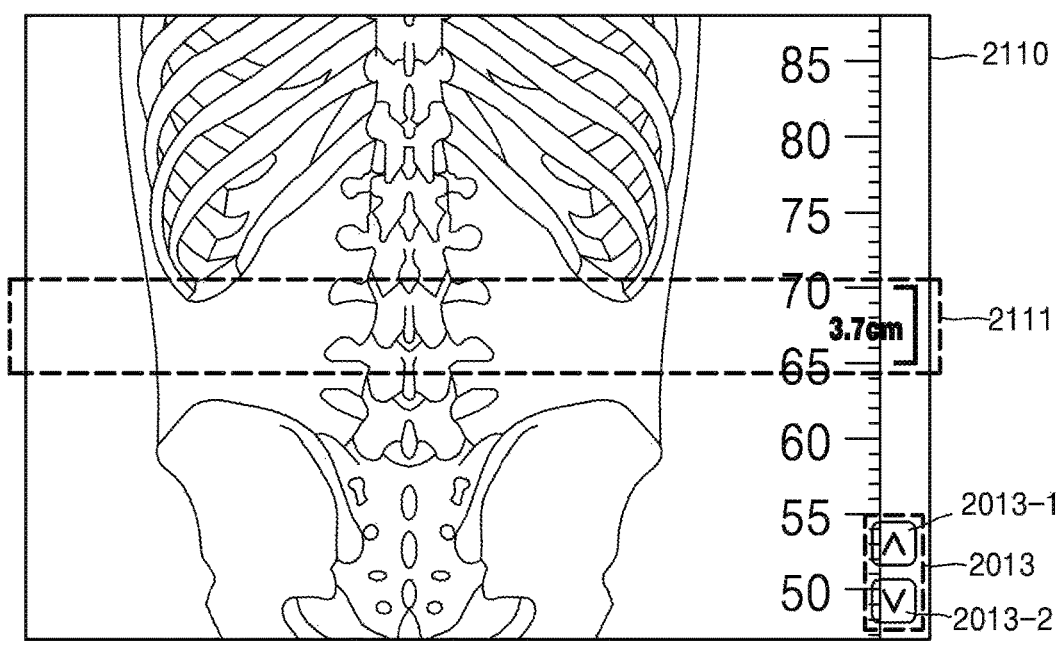

When receiving a user input regarding the user interface 2013 illustrated in FIG. 20, the apparatus 100 for displaying a medical image may display a synthesis image 2110 magnified based on another overlapped region 2111 selected from among the plurality of overlapped regions as illustrated in FIG. 21.

For example, the user interface 2013 may include a button 2013-1 for moving to an overlapped region located above an overlapped region currently being displayed, and a button 2013-2 for moving to an overlapped region located below the overlapped region currently being displayed.

When receiving a user input that selects the button 2013-1, the apparatus 100 for displaying a medical image may select an overlapped region located above the second overlapped region from among the plurality of overlapped regions. When receiving a user input that selects the button 2013-2, the apparatus 100 for displaying a medical image may select an overlapped region located below the second overlapped region from among the plurality of overlapped regions.

Alternatively, the apparatus 100 for displaying a medical image may determine a sequence of an overlapped region to be displayed based on the synthesis accuracy of the overlapped region. For example, when receiving a user input that selects the display mode for observing an overlapped region, the apparatus 100 for displaying a medical image may display a synthesis image magnified based on an overlapped region having lowest synthesis accuracy. When receiving a user input for moving to another overlapped region, the apparatus 100 for displaying a medical image may select an overlapped region having the next high synthesis accuracy after an overlapped region currently being displayed, and magnify the synthesis image based on the selected overlapped region.

Meanwhile, the user may determine to manually synthesize images with respect to a synthesis image having low synthesis accuracy.

Figure 22:
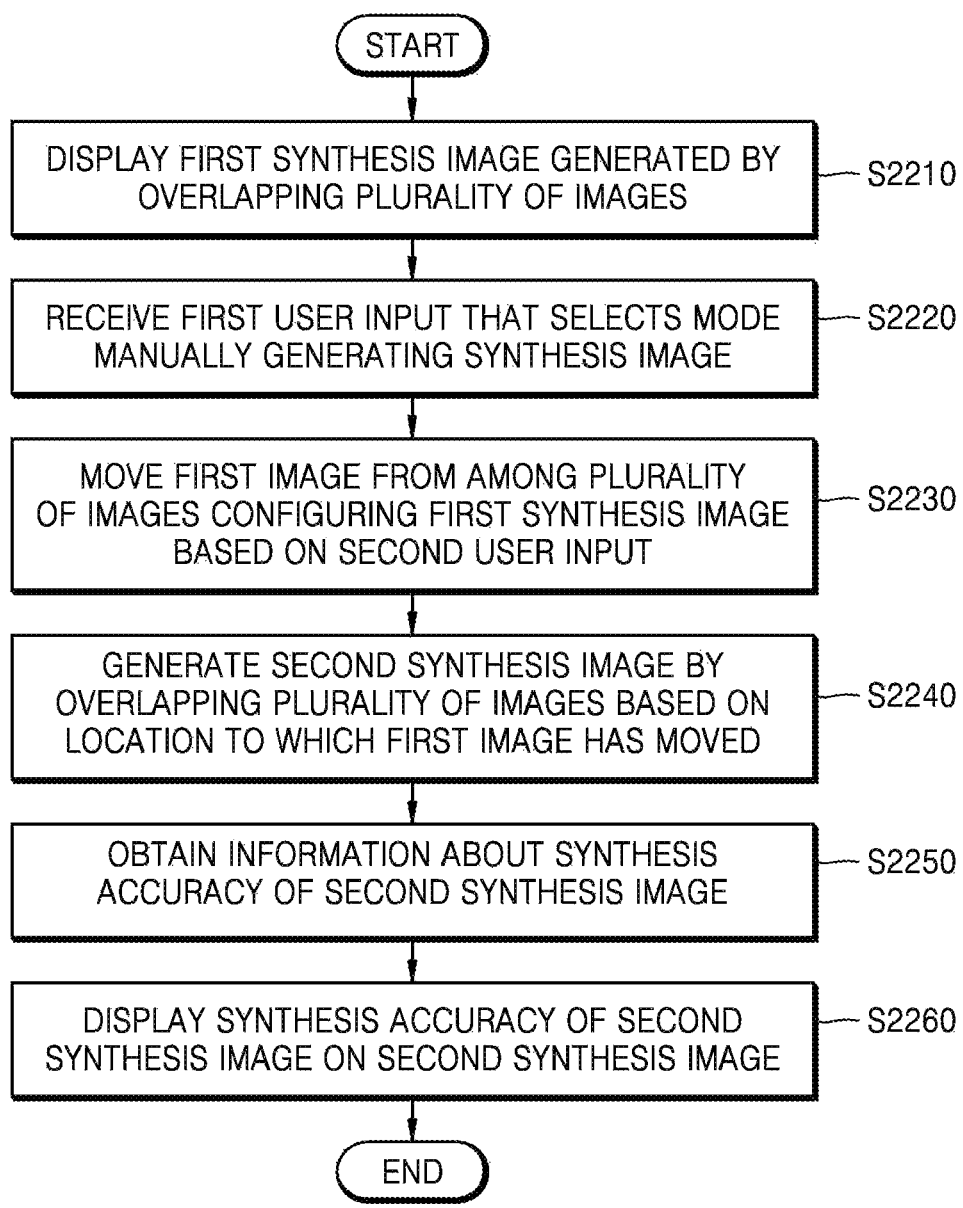
FIG. 22 is a flowchart illustrating a method of operating an apparatus for displaying a medical image in a mode that manually generates a synthesis image, according to an embodiment.

FIG. 22 is a flowchart illustrating a method of operating an apparatus for displaying a medical image in a mode that manually generates a synthesis image according to an embodiment.

In operation S2210, the apparatus 100 for displaying a medical image may display a first synthesis image generated by overlapping a plurality of images. The apparatus 100 for displaying a medical image may display information about synthesis accuracy of the first synthesis image on the synthesis image. Since operation S2210 corresponds to operation S640 of FIG. 6, repeated description is omitted.

In operation S2220, the apparatus 100 for displaying a medical image may receive a first user input that selects a mode manually generating a synthesis image.

Figure 23:
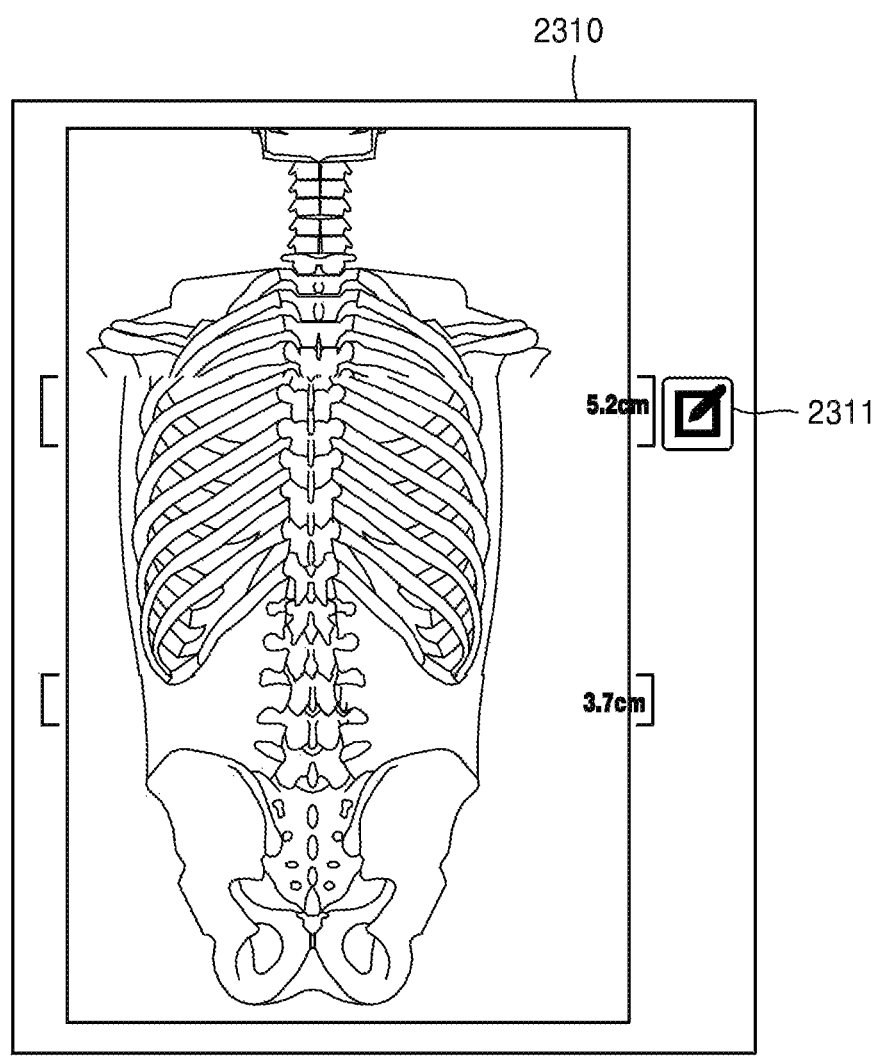
FIGS. 23 and 24 are diagrams illustrating an example of a synthesis image and a user interface displayed by an apparatus for displaying a medical image that operates in a mode that manually generates a synthesis image according to an embodiment.

As illustrated in FIG. 23, the apparatus 100 for displaying a medical image may display a synthesis image 2310 and an icon 2311 for executing the mode manually generating a synthesis image together.

A user who uses the apparatus 100 for displaying a medical image according to an embodiment may determine to manually synthesize images with respect to an overlapped region having low synthesis accuracy. Therefore, in the case where a synthesis image includes a plurality of overlapped regions, the apparatus 100 for displaying a medical image may display the icon 2311 for executing the mode manually generating a synthesis image in the neighborhood of an overlapped region having lowest synthesis accuracy. Alternatively, the apparatus 100 for displaying a medical image may display the icon 2311 for executing the mode manually generating a synthesis image in the neighborhood of an overlapped region having synthesis accuracy lower than a threshold value. Alternatively, the apparatus 100 for displaying a medical image may display the icon 2311 for executing the mode manually generating a synthesis image in the neighborhood of an overlapped region for which it is determined that synthesis has failed.

When receiving a user input that selects the icon 2311, the apparatus 100 for displaying a medical image may execute the mode manually generating a synthesis image.

Figure 24:
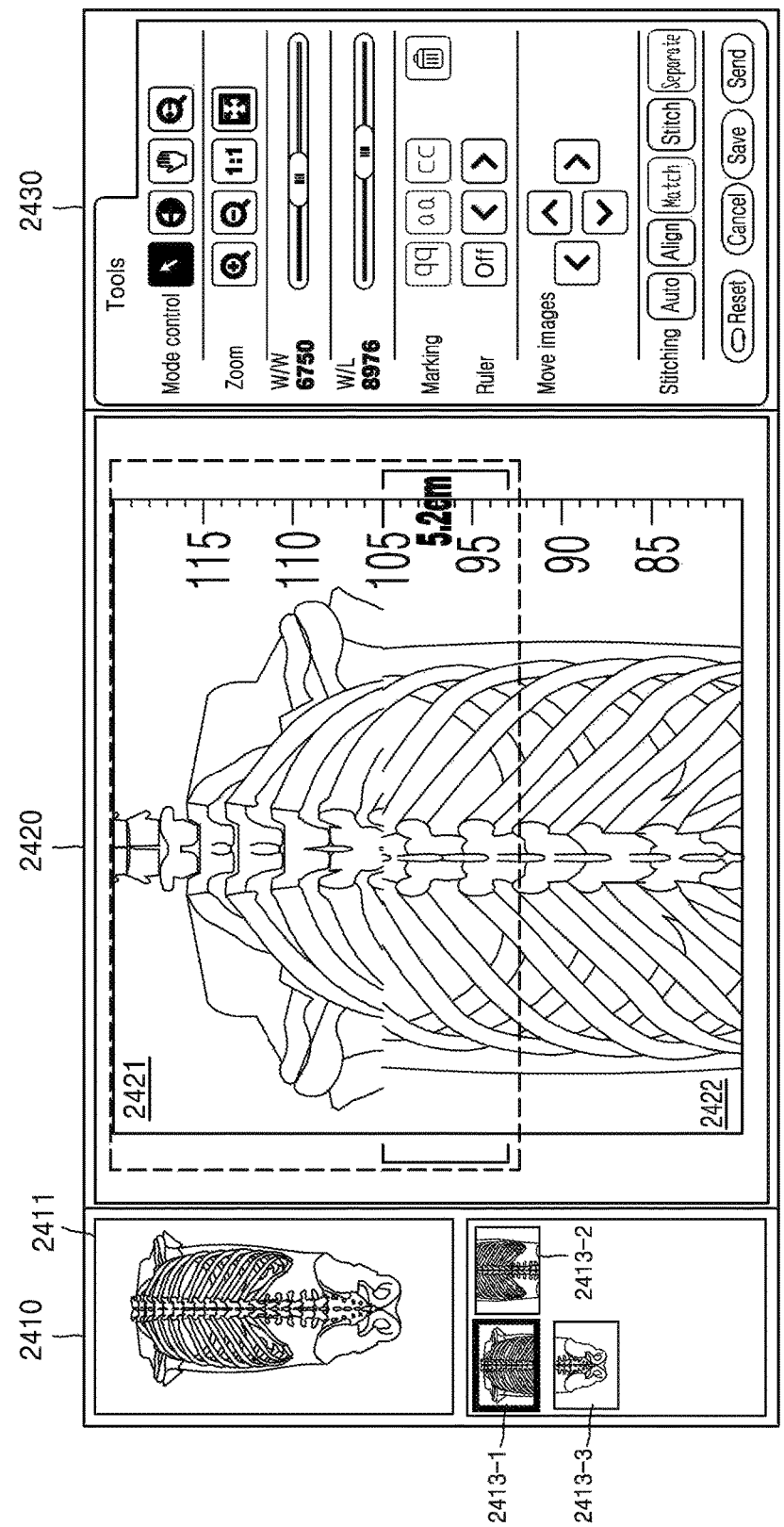

As illustrated in FIG. 24, when the mode manually generating a synthesis image is executed, the apparatus 100 for displaying a medical image may magnify a synthesis image based on a first overlapped region from among a plurality of overlapped regions of a synthesis image.

The apparatus 100 for displaying a medical image may display a synthesis image magnified based on the first overlapped region in which a first image 2421 overlaps a second image 2422 within a predetermined region 2420. The apparatus 100 for displaying a medical image may display a tool bar 2430 for controlling the first image 2421 and the second image 2422 in a region different from the region 2420. The tool bar 2430 is an interface provided to a user, and the user may input a user input to the tool bar 2430 by using a user input unit.

In operation S2230, the apparatus 100 for displaying a medical image may move a first image from among a plurality of images configuring a first synthesis image based on a second user input. In operation S2240, the apparatus 100 for displaying a medical image may generate a second synthesis image by overlapping a plurality of images based on a location to which the first image has moved.

As illustrated in FIG. 24, when the mode manually generating a synthesis image is executed, the apparatus 100 for displaying a medical image may display a plurality of images 2413-1, 2413-2, and 2413-3 configuring a synthesis image 2411 within a predetermined region 2410.

When receiving a user input that selects the first image 2413-1 from among the plurality of images 2413-1, 2413-2, and 2413-3, the apparatus 100 for displaying a medical image may move the location of the first image 2413-1 within the synthesis image. The apparatus 100 for displaying a medical image may receive a user input that moves the location of a first image 2421 corresponding to the selected first image 2413-1. As the first image 2421 moves based on the user input, the width of a region in which the first image 2421 overlaps the second image 2422 may change.

The apparatus 100 for displaying a medical image may regenerate a synthesis image by overlapping the first image and the second image based on the location to which the first image has moved according to the user input.

In operation S2250, the apparatus 100 for displaying a medical image may obtain information about synthesis accuracy of the second synthesis image. In operation S2260, the apparatus 100 for displaying a medical image may display the synthesis accuracy with respect to the second synthesis image on the second synthesis image. Operations S2250 and S2260 of FIG. 22 may correspond to operations S630 and S640 of FIG. 6, respectively. Descriptions repeated in FIG. 6 are omitted.

The apparatus 100 for displaying a medical image according to an embodiment may allow a user to determine whether image stitching has been accurately performed by providing information about the synthesis accuracy of a synthesis image even in the case where the synthesis image has been manually generated by a user.

Figure 25:
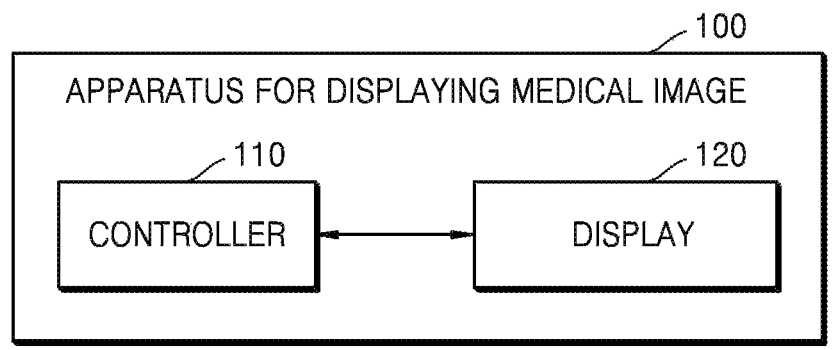
FIGS. 25 and 26 are block diagrams illustrating an apparatus for displaying a medical image, according to an embodiment.
Figure 26:
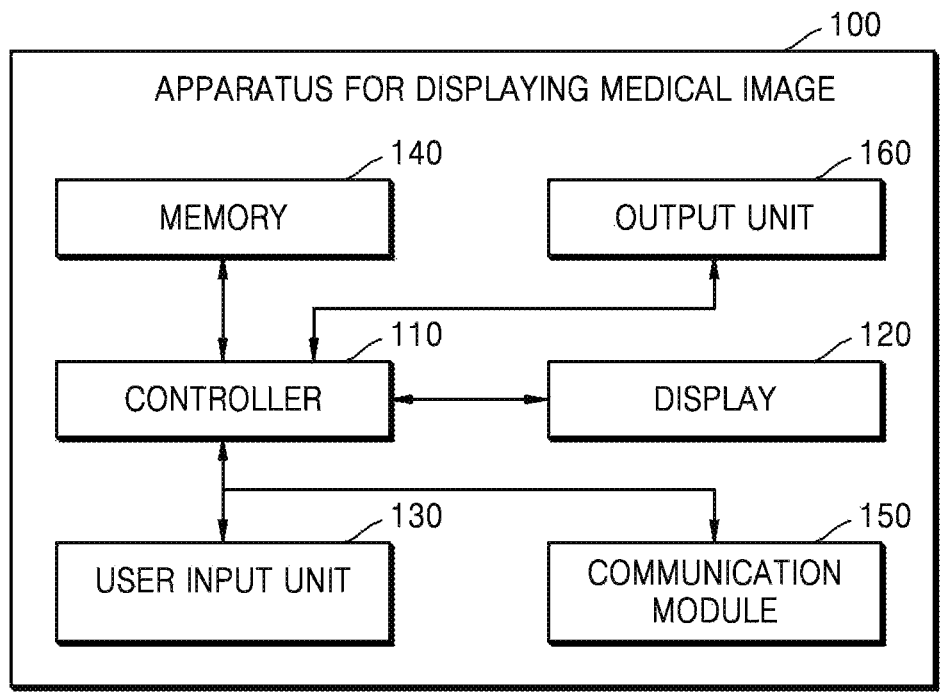

FIGS. 25 and 26 are block diagrams illustrating the apparatus 100 for displaying a medical image according to an embodiment.

Each operation of the methods illustrated in FIGS. 6, 7A, 12, 18, and 22 may be performed by components of the apparatus 100 for displaying a medical image illustrated in FIG. 25 or 26, and descriptions repeated by those of FIGS. 6, 7A, 12, 18, and 22 are omitted.

As illustrated in FIG. 25, the apparatus 100 for displaying a medical image may include a controller 110 and a display 120.

The controller 110 controls an overall operation of the apparatus 100 for displaying a medical image. For example, the controller 110 may control the display 120. As illustrated in FIG. 26, in the case where the apparatus 100 for displaying a medical image is implemented by more components, the controller 110 may further control at least one of a user input unit 130, a memory 140, a communication module 150, and an output unit 160.

The controller 110 may include an image obtainer (not shown) for obtaining an image of an object, a location obtainer (not shown) for obtaining location information of an image or location information of an apparatus for obtaining an image, a data processor (not shown) for synthesizing a plurality of images and calculating synthesis accuracy of a synthesis image, and a user interface provider (not shown) for displaying a user interface related to a synthesis image.

The controller 110 may generate a synthesis image by obtaining a first image and a second image that are image of the same region of an object repeatedly captured, and overlapping a first overlapped region of the first image and a second overlapped region of the second image. The controller 110 may obtain information about synthesis accuracy representing a degree in which a first portion of the object represented by the first overlapped region coincides with a second portion of the object represented by the second overlapped region. The controller 110 may control the display 120 to display the information about the synthesis accuracy and the synthesis image.

The display 120 may display information processed by the apparatus 100 for displaying a medical image. For example, the display 120 may display a medical image, or display a user interface related to the medical image.

To display information processed by the apparatus 100 for displaying a medical image, the display 120 may include at least one of a liquid crystal display, a thin film transistor-liquid crystal display, an organic light-emitting diode, a flexible display, a 3 dimensional (3D) display, and an electrophoretic display.

The display 120 may be configured in the form of a touchscreen forming a layered structure with a touchpad.

The display 120 may display a plurality of images of a plurality of regions of an object. The display 120 may display a ruler image representing information about the location of each of the plurality of images on each image.

The display 120 may display a synthesis image generated by overlapping a plurality of images. The display 120 may display information about synthesis accuracy of a synthesis image on the synthesis image generated by the controller 110.

Meanwhile, the apparatus 100 for displaying a medical image according to an embodiment may be implemented by more components than the components illustrated in FIG. 25. For example, as illustrated in FIG. 26, the apparatus 100 for displaying a medical image according to an embodiment may further include at least one of the user input unit 130, the memory 140, the communication module 150, and the output unit 160.

The user input unit 130 denotes means for inputting data for allowing a user to control the apparatus 100 for displaying a medical image. For example, the user input unit 130 may include a keypad, a dome switch, a button, a wheel, a track ball, a touchpad, a jog wheel, a jog switch, etc., but is not limited thereto.

The user input unit 130 may receive at least one of a user input for setting a parameter related to a medical image, a user input for controlling an operation of the apparatus 100 for displaying a medical image, a user input for controlling an external device or a server connected with the apparatus 100 for displaying a medical image, and a user input for inputting information about a medical image.

The user input unit 130 may receive a user input that selects a method of displaying the information about the synthesis accuracy of the synthesis image. Also, the user input unit 130 may receive a user input that selects the display mode for observing an overlapped region of the synthesis image or the mode manually generating a synthesis image. The user input unit 130 may receive a user input for manually generating a synthesis image.

The memory 140 may store a program for processing or controlling of the controller 110, and store data input to the apparatus 100 for displaying a medical image or output from the apparatus 100 for displaying a medical image. For example, the memory 140 may store a medical image displayed via the apparatus 100 for displaying a medical image.

The memory 140 may include at least one storage medium from among a flash memory type, a hard disk type, a multimedia card micro type, a card type memory (for example, a secure digital (SD) memory or an extreme digital (XD) memory, etc.), random access memory (RAM), static random access memory (SRAM), read-only memory (ROM), electrically erasable programmable read-only memory (EEPROM), programmable read-only memory (PROM), a magnetic memory, a magnetic disk, and an optical disk.

Programs stored in the memory 140 may be divided into a plurality of modules depending on a function thereof, for example, divided into a user interface (UI) module, a notice module, etc.

The memory 140 may store a plurality of images of a plurality of regions of an object, and a synthesis image that synthesizes a plurality of images. The memory 140 may store location information of each of the plurality of images, or information about synthesis accuracy of a synthesis image.

The communication module 150 may include one or more components that enable communication between the apparatus 100 for displaying a medical image and the apparatus for obtaining a medical image or the server.

The communication module 150 may connect various devices that provide medical image data regarding an object with the apparatus 100 for displaying a medical image via a wired line or wirelessly.

The communication module 150 may receive medical image data from the apparatus for obtaining a medical image that obtains the medical image data from an object. Also, the communication module 150 may transmit a control signal to the apparatus for obtaining a medical image.

The communication module 150 may receive medical image data from the server.

The communication module 150 may give/take medical image data to/from a hospital server connected via a picture archiving and communication system (PACS)

The communication module 150 may perform data communication with the server according to a standard of digital imaging and communications in medicine (DICOM).

The output unit 160 may output information processed by the apparatus 100 for displaying a medical image. For example, the output unit 160 may output an audio signal, a video signal, a light signal, or a vibration signal. The output unit 160 may output a video signal by including a display separated from the display 120.

The output unit 160 may output an audio signal received from the communication module 150 or stored in the memory 140. Also, the output unit 160 may output an audio signal related to a function (for example, a message reception note and a notice note) performed by the apparatus 100 for displaying a medical image. The output unit 160 may include a speaker, a buzzer, etc. in order to output an audio signal. Also, the output unit 160 may output a vibration signal.

Meanwhile, the apparatus 100 for displaying a medical image according to an embodiment may be connected with an X-ray system or may be included in the X-ray system.

Figure 27:
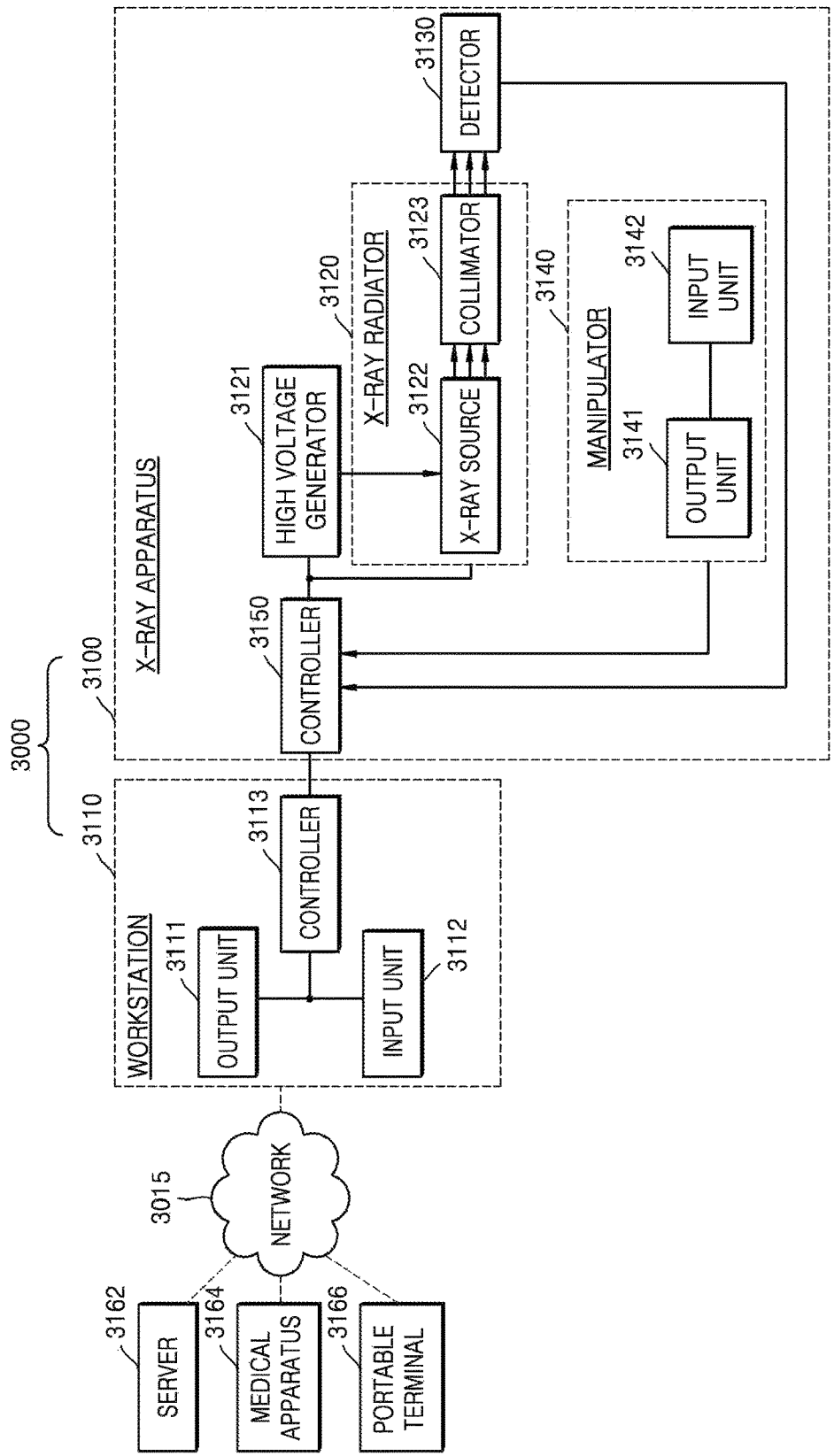
FIG. 27 is a block diagram illustrating a general X-ray system.

FIG. 27 is a block diagram of a X-ray system.

Referring to FIG. 27, the X-ray system 3000 includes an X-ray apparatus 3100 and a workstation 3110. The X-ray apparatus 3100 shown in FIG. 27 may be a fixed-type X-ray apparatus or a mobile X-ray apparatus. The X-ray apparatus 3100 may include an X-ray radiator 3120, a high voltage generator 3121, a detector 3130, a manipulator 3140, and a controller 3150. The controller 3150 may control overall operations of the X-ray apparatus 3100.

The high voltage generator 3121 generates a high voltage for generating X-rays, and applies the high voltage to an X-ray source 3122.

The X-ray radiator 3120 includes the X-ray source 3122 receiving the high voltage from the high voltage generator 3121 to generate and radiate X-rays, and a collimator 3123 for guiding a path of the X-ray radiated from the X-ray source 3122 and adjusting an irradiation region radiated by the X-ray.

The X-ray source 3122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 3121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 3130 detects an X-ray that is radiated from the X-ray radiator 3120 and has been transmitted through an object. The detector 3130 may be a digital detector. The detector 3130 may be implemented by using a thin film transistor (TFT) or a charge coupled device (CCD). Although the detector 3130 is included in the X-ray apparatus 3100 in FIG. 27, the detector 3130 may be an X-ray detector that is a separate device capable of being connected to or separated from the X-ray apparatus 3100.

The X-ray apparatus 3100 may further include a manipulator 3140 for providing a user with an interface for manipulating the X-ray apparatus 3100. The manipulator 3140 may include an output unit 3141 and an input unit 3142. The input unit 3142 may receive from a user a command for manipulating the X-ray apparatus 3100 and various types of information related to X-ray imaging. The controller 3150 may control or manipulate the X-ray apparatus 3100 according to the information received by the input unit 3142. The output unit 3141 may output sound representing information related to a imaging operation such as the X-ray radiation under the control of the controller 3150.

The workstation 3110 and the X-ray apparatus 3100 may be connected to each other by wire or wirelessly. When they are connected to each other wirelessly, a device (not shown) for synchronizing clock signals with each other may be further included. The workstation 3110 and the X-ray apparatus 3100 may exist within physically separate spaces.

The workstation 3110 may include an output unit 3111, an input unit 3112, and a controller 3113. The output unit 3111 and the input unit 3112 provide a user with an interface for manipulating the workstation 3110 and the X-ray apparatus 3100. The controller 3113 may control the workstation 3110 and the X-ray apparatus 3100.

The X-ray apparatus 3100 may be controlled via the workstation 3110 or may be controlled by the controller 3150 included in the X-ray apparatus 3100. Accordingly, a user may control the X-ray apparatus 3100 via the workstation 3110 or may control the X-ray apparatus 3100 via the manipulator 3140 and the controller 3150 included in the X-ray apparatus 3100. In other words, a user may remotely control the X-ray apparatus 3100 via the workstation 3110 or may directly control the X-ray apparatus 3100.

Although the controller 3113 of the workstation 3110 is separate from the controller 3150 of the X-ray apparatus 3100 in FIG. 1, FIG. 1 is only an example. In some embodiments, the controllers 3113 and 3150 may be integrated into a single controller, and the single controller may be included in only one of the workstation 3110 and the X-ray apparatus 3100. Hereinafter, the controllers 3113 and 3150 may denote the controller 3113 of the workstation 3110 and/or the controller 3150 of the X-ray apparatus 3100.

The output unit 3111 and the input unit 3112 of the workstation 3110 may provide a user with an interface for manipulating the X-ray apparatus 3100, and the output unit 3141 and the input unit 3142 of the X-ray apparatus 3100 may also provide a user with an interface for manipulating the X-ray apparatus 100. Although the workstation 3110 and the X-ray radiation apparatus 3100 include the output units 3111 and 3141, respectively, and the input units 3112 and 3142, respectively, in FIG. 1, embodiments are not limited thereto. Only one of the workstation 3110 and the X-ray apparatus 3100 may include an output unit or an input unit.

Hereinafter, the input units 3112 and 3142 may denote the input unit 3112 of the workstation 3110 and/or the input unit 3142 of the X-ray apparatus 3100, and the output units 3111 and 3141 may denote the output unit 3111 of the workstation 3110 and/or the output unit 3141 of the X-ray apparatus 3100.

Examples of the input units 3112 and 3142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 3112 and 3142, and the input units 3112 and 3142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 3113 and 3150 generate signals corresponding to the commands input through the switch manipulation, that is, a prepare signal, and transmit the generated signals to the high voltage generator 3121 generating a high voltage for generating the X-ray.

When the high voltage generator 3121 receives the prepare signal from the controllers 3113 and 3150, the high voltage generator 121 starts a pre-heating operation, and when the pre-heating is finished, the high voltage generator 121 outputs a ready signal to the controllers 3113 and 3150. In addition, the detector 3130 also needs to prepare to detect the X-ray, and thus the high voltage generator 3121 performs the pre-heating operation and the controllers 3113 and 3150 transmit a prepare signal to the detector 3130 so that the detector 3130 may prepare to detect the X-ray transmitted through the object. The detector 3130 prepares to detect the X-ray in response to the prepare signal, and when the preparing for the detection is finished, the detector 130 outputs a ready signal to the controllers 3113 and 3150.

When the pre-heating operation of the high voltage generator 3121 is finished and the detector 3130 is ready to detect the X-ray, the controllers 3113 and 3150 transmit a radiation signal to the high voltage generator 3121, the high voltage generator 3121 generates and applies the high voltage to the X-ray source 3122, and the X-ray source 3122 radiates the X-ray.

When the controllers 3113 and 3150 transmit the radiation signal to the high voltage generator 121, the controllers 113 and 150 may transmit a sound output signal to the output units 3111 and 3141 so that the output units 3111 and 3141 output a predetermined sound and the object may recognize the radiation of the X-ray. The output units 3111 and 3141 may also output a sound representing information related to photographing in addition to the X-ray radiation. In FIG. 27, the output unit 3141 is included in the manipulator 3140; however, the embodiments are not limited thereto, and the output unit 3141 or a portion of the output unit 3141 may be located elsewhere. For example, the output unit 141 may be located on a wall of an examination room in which the X-ray photographing of the object is performed.

The controllers 3113 and 3150 control locations of the X-ray radiator 3120 and the detector 3130, photographing timing, and photographing conditions, according to photographing conditions set by the user.

In more detail, the controllers 3113 and 3150 control the high voltage generator 3121 and the detector 3130 according to the command input via the input units 3112 and 3142 so as to control radiation timing of the X-ray, an intensity of the X-ray, and a region radiated by the X-ray. In addition, the control units 3113 and 3150 adjust the location of the detector 3130 according to a predetermined photographing condition, and controls operation timing of the detector 3130.

Furthermore, the controllers 3113 and 3150 generate a medical image of the object by using image data received via the detector 3130. In detail, the controllers 3113 and 3150 may receive the image data from the detector 3130, and then, generate the medical image of the object by removing noise from the image data and adjusting a dynamic range and interleaving of the image data.

The output units 3111 and 3141 may output the medical image generated by the controllers 3113 and 3150. The output units 3111 and 3141 may output information that is necessary for the user to manipulate the X-ray apparatus 3100, for example, a user interface (UI), user information, or object information. Examples of the output units 3111 and 3141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 3110 shown in FIG. 27 may further include a communicator (not shown) that may be connected to a server 3162, a medical apparatus 3164, and a portable terminal 3166 via a network 3015.

The communicator may be connected to the network 3015 by wire or wirelessly to communicate with the server 3162, the medical apparatus 3164, or the portable terminal 3166. The communicator may transmit or receive data related to diagnosis of the object via the network 3015, and may also transmit or receive medical images captured by the medical apparatus 3164, for example, a CT apparatus, an MRI apparatus, or an X-ray apparatus. Moreover, the communicator may receive a medical history or treatment schedule of an object (e.g., a patient) from the server 3162 to diagnose a disease of the object. Also, the communicator may perform data communication with the portable terminal 3166 such as a mobile phone, a personal digital assistant (PDA), or a laptop computer of a medical doctor or a client, as well as the server 3162 or the medical apparatus 3164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, W-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 3100 shown in FIG. 27 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 3110 and the X-ray apparatus 3100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

In the case where the apparatus 100 for displaying a medical image is included in the X-ray system 3000, the apparatus 100 for displaying a medical image may perform all or a portion of a function performed by at least one of the output unit 3111, the input unit 3112, and the controller 3113 of the workstation 3110 of FIG. 27.

Alternatively, the apparatus 100 for displaying a medical image according to an embodiment is an apparatus separated from the X-ray system 3000, and may be connected with the X-ray system 3000 via a wired line or wirelessly and receive an X-ray image from the X-ray system 3000.

Various embodiments may be also implemented in the form of a recording medium including a command executable by a computer such as a program module executed by a computer. A non-transitory computer-readable recording medium may be an arbitrary available medium accessible by a computer, and includes all of volatile and non-volatile media, and separated type and non-separated type media. Also, the non-transitory computer-readable recording medium may include both a computer storage medium and a communication medium. The computer storage medium includes all of volatile and non-volatile, separated type and non-separated type media implemented by using an arbitrary method or technology for storing information such as a computer-readable command, a data structure, a program module, or other data. The communication medium typically includes a computer-readable command, a data structure, or other data regarding a modulated data signal such as a program module, or other transmission mechanisms, and includes an arbitrary information transfer medium.

Description of an embodiment is provided for an exemplary purpose, and a person of ordinary skill in the art will understand that other specific modifications may be easily made therein without departing from the technical spirit or essential characteristics of the inventive concept. Therefore, the above embodiments are exemplary in all aspects and should be understood as not being limited thereto. For example, each component described as a single form may be embodied in a distributed fashion, and likewise, components described as being distributed may be embodied in a combined form.

It should be construed that all changes and modifications derived from the meaning and range of claims and an equivalent concept thereof are included in the range of the inventive concept.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of displaying a medical image, the method comprising:
    obtaining a first image of a first region of an object;
    obtaining a second image of a second region, different from the first region, of the object, wherein the first and second images are images captured by using an X-ray, and the first region has an overlap with the second region;
    generating a synthesis image by overlapping a first image region of the first image and a second image region of the second image;
    obtaining first information about synthesis accuracy, the synthesis accuracy representing a degree to which the first image region and the second image region coincide with each other in representing a portion of the object within the overlap of the first region with the second region;
    comparing the synthesis accuracy with a threshold value; and
    when the synthesis accuracy is lower than the threshold value, displaying a screen including the synthesis image and an icon, which is displayed on a region corresponding to an overlapping region of the synthesis image in which the first image region of the first image is overlapped with the second image region of the second image, for executing a mode manually generating a synthesis image.

2. The method of claim 1, wherein
    the generating generates the synthesis image such that the first and second images overlap by an overlap width in the synthesis image, and
    the obtaining of the first information about the synthesis accuracy comprises obtaining the first information about the synthesis accuracy by comparing the overlap width with a reference value.

3. The method of claim 2, wherein
    the first image comprises a first ruler image indicating distances from a reference point to portions of the object displayed in the first image,
    the second image comprises a second ruler image indicating distances from the reference point to portions of the object displayed in the second image, and
    the obtaining of the first information about the synthesis accuracy further comprises determining the reference value by:
        obtaining a first distance value, displayed by the first ruler image, indicating a distance between the reference point and a location on a side of the first image corresponding to one boundary of a region of the synthesis image in which the first image overlaps the second image, based on the first ruler image,
        obtaining a second distance value, displayed by the second ruler image, indicating a distance between the reference point and a location on a side of the second image corresponding to another boundary of the region of the synthesis image, based on the second ruler image; and
        determining a difference between the first distance value and the second distance value as the reference value.

4. The method of claim 1, wherein the obtaining of the first information about the synthesis accuracy further comprises:
    determining a similarity between the first image region and the second image region as the first information about the synthesis accuracy by comparing the first image region with the second image region.

5. The method of claim 1, wherein the generating of the synthesis image further comprises:
    displaying the first image comprising a first ruler image indicating distances from a reference point to portions of the object displayed in the first image;
    displaying the second image comprising a second ruler image indicating distances from the reference point to portions of the object displayed in the second image;
    comparing at least a portion of the first image with at least a portion of the second image based on the first ruler image and the second ruler image;
    determining the first image region and the second image region based on a similarity between at least the portion of the first image with at least the portion of the second image; and
    generating the synthesis image by overlapping the determined first image region of the first image and the determined second image region of the second image.

6. The method of claim 1, further comprising:
    displaying the first information about the synthesis accuracy and the synthesis image together,
    wherein the displaying of the first information comprises displaying a marker, comprising at least one of a color, a pattern, a figure, a contrast, and a numerical value corresponding to the synthesis accuracy, on a region of the synthesis image in which the first image overlaps the second image.

7. The method of claim 1 further comprising:
    displaying the first information about the synthesis accuracy and the synthesis image together,
    wherein the displaying of the first information comprises:
    displaying the first information about the synthesis accuracy according to a method selected based on a user input.

8. The method of claim 1, wherein
    the generating generates the synthesis image so that the first and second images overlap by an overlap width in the synthesis image, and
    the method further comprises displaying the overlap width.

9. The method of claim 1, wherein
    the generating of the synthesis image comprises generating the synthesis image by overlapping a plurality of images comprising the first image and the second image, and
    the method further comprises:
        receiving a first user input of selecting a display mode for observing a plurality of overlapped image regions in which the plurality of images overlap in order to generate the synthesis image; and
        magnifying the synthesis image based on a first overlapped image region from among the plurality of overlapped image regions.

10. The method of claim 9, further comprising:
receiving a second user input for moving between the plurality of overlapped image regions;
selecting a second overlapped image region from among the plurality of overlapped image regions based on the second user input; and
magnifying the synthesis image based on the second overlapped image region.

11. The method of claim 1, further comprising:
moving a location of the first image from among the first image and the second image configuring the synthesis image based on a user input;
regenerating a synthesis image by overlapping the first image and the second image based on a location to which the first image has moved;
obtaining third information about synthesis accuracy with respect to the regenerated synthesis image; and
displaying the obtained third information about synthesis accuracy with respect to the regenerated synthesis image on the regenerated synthesis image.

12. A non-transitory computer-readable recording medium having recorded thereon a program that, when executed by at least one hardware processor, causes the one hardware processor to perform the method of claim 1.

13. An apparatus for displaying a medical image, the apparatus comprising:
a processor configured to:
obtain a first image of a first region of an object,
obtain a second image of a second region, different from the first region, of the object, wherein the first and second images are images captured by using an X-ray, and the first region has an overlap with the second region,
generate a synthesis image by overlapping a first image region of the first region and a second image region of the second region,
obtain first information about synthesis accuracy, the synthesis accuracy representing a degree to which the first image region and the second image region coincide with each other in representing a portion of the object within the overlap of the first region with the second region;
compare the synthesis accuracy with a threshold value; and
a display configured to display a screen,
wherein, when the synthesis accuracy is lower than the threshold value, the processor is further configured to control the display to display the synthesis image and an icon, which is displayed on a region corresponding to an overlapping region of the synthesis image in which the first image region of the first image is overlapped with the second image region of the second image, for executing a mode manually generating a synthesis image.

14. The apparatus of claim 13, wherein
the processor generates the synthesis image so that the first and second images overlap by an overlap width in the synthesis image, and
the processor is further configured to obtain the first information about the synthesis accuracy by comparing the overlap width with a reference value.

15. The apparatus of claim 14, wherein
the first image comprises a first ruler image indicating distances from a reference point to portions of the object displayed in the first image,
the second image comprises a second ruler image indicating distances from the reference point to portions of the object displayed in the second image, and
the processor is further configured to:
obtain a first distance value, displayed by the first ruler image, indicating a distance between the reference point and a location on one a side of the first image corresponding to one boundary of a region of the synthesis image in which the first image overlaps the second image, based on the first ruler image,
obtain a second distance value, displayed by the second ruler image, indicating a distance between the reference point and a location on a side of the second image corresponding to another boundary of the region of the synthesis image, based on the second ruler image, and
determine a difference between the first distance value and the second distance value as the reference value.

16. The apparatus of claim 13, wherein the processor is further configured to determine a similarity between the first image region and the second image region as the first information about the synthesis accuracy by comparing the first image region with the second image region.

17. The apparatus of claim 13, wherein the processor is further configured to
control the display to display the first image comprising a first ruler image indicating distances from a reference point to portions of the object displayed in the first image, and display the second image comprising a second ruler image indicating distances from the reference point to portions of the object displayed in the second image,
compare at least a portion of the first image with at least a portion of the second image based on the first ruler image and the second ruler image,
determine the first image region and the second image region based on a similarity between at least the portion of the first image with at least the portion of the second image, and
generate the synthesis image by overlapping the determined first image region of the first image and the determined second image region of the second image.

18. The apparatus of claim 13, wherein the display is further configured to display a marker comprising at least one of a color, a pattern, a figure, a contrast, and a numerical value corresponding to the synthesis accuracy on a region of the synthesis image formed by the overlapping the first image region and the second image region in order to generate the synthesis image.

* * * * *